(12) United States Patent
Tamura et al.

(10) Patent No.: US 6,168,924 B1
(45) Date of Patent: *Jan. 2, 2001

(54) LIMULUS REACTION-ACTIVATING SUBSTANCE, METHOD FOR INACTIVATING THE SUBSTANCE AND MEASURING ITS AMOUNT, AND METHOD FOR MEASURING LIMULUS REACTION

(75) Inventors: Hiroshi Tamura, Musashimurayama; Shigenori Tanaka, Kodaira; Maki Watanabe, Tokyo, all of (JP)

(73) Assignee: Seikagaku Kogyo Kabushiki Kaisha, Tokyo (JP)

( * ) Notice: Under 35 U.S.C. 154(b), the term of this patent shall be extended for 0 days.

This patent is subject to a terminal disclaimer.

(21) Appl. No.: 08/954,792

(22) Filed: Oct. 21, 1997

(30) Foreign Application Priority Data

Oct. 21, 1996 (JP) .................................. 8-298186

(51) Int. Cl.[7] ...................... G01N 33/53; G01N 1/00; C12Q 1/37; C12N 9/99
(52) U.S. Cl. ................... 435/7.1; 435/4; 435/13; 435/18; 435/19; 435/23; 435/24; 435/38; 435/175; 435/183; 435/184; 436/175; 436/825
(58) Field of Search ................... 435/4, 7.1, 13, 435/18, 19, 23, 24, 38, 175, 183, 184; 436/175, 825

(56) References Cited

U.S. PATENT DOCUMENTS

| | | | |
|---|---|---|---|
| 4,495,294 | 1/1985 | Nakahara et al. | 436/502 |
| 5,155,032 | 10/1992 | Tanaka et al. | 435/184 |
| 5,179,006 | 1/1993 | Matuura et al. | 435/23 |
| 5,266,461 | 11/1993 | Tanaka | 435/7.21 |
| 5,286,625 | * 2/1994 | Tanaka et al. | 435/18 |
| 5,378,610 | * 1/1995 | Tanaka et al. | 435/18 |
| 5,389,547 | 2/1995 | Tanaka et al. | 436/94 |
| 5,401,647 | 3/1995 | Tanaka et al. | 435/176 |
| 5,476,772 | 12/1995 | Tsuchiya et al. | 435/23 |
| 5,648,230 | * 7/1997 | Tamura et al. | 435/18 |

FOREIGN PATENT DOCUMENTS

| | | | |
|---|---|---|---|
| B56406/94 | 9/1994 | (AU) | G01N 33/579 |
| 0 513 361 A1 | 11/1992 | (EP) | G01N 33/579 |
| 0 569 033 A2 | 11/1993 | (EP) | G01N 33/579 |

OTHER PUBLICATIONS

Hiroshi Tamura, et al., A New Sensitive Microplate Assay of Plasma Endotoxin, Journal of Clinical Laboratory Analysis 6:232–238(1992).

Hiroshi Fujikawa, et al., Clearance of Endotoxin from Blood of Rabbits Injected with Staphylococcal Toxic Shock Syndrome Toxin–1, Infection and Immunity, vol. 52, No. 1, Apr. 1986, p. 134–137.

* cited by examiner

Primary Examiner—Rodney P. Swartz
(74) Attorney, Agent, or Firm—Knobbe, Marten, Olson & Bear, LLP

(57) ABSTRACT

The presence of endotoxin in the outer membrane of cell wall of a Gram-negative bacteria is used to determine bacterial contamination in a biological product. The amount of endotoxin present in a biological product is accurately measured without influence of a limulus reaction-activating substance which causes a false-positive reaction, by a method including the steps of: inactivating the limulus reaction-activating substance, if any, in the biological product, by exposing the biological product to a surfactant at a temperature ranging from the surfactant's freezing point to 50° C.; and measuring the amount of endotoxin present in the biological product, using a limulus reagent.

14 Claims, 10 Drawing Sheets

O ...dd Water's dilution after Brij 56's addition
■ ...Brij's addition after dd water's dilution
△ ...Brij's dilution after Brij's 56's addition O ...dd Water's dilution after Brij 56's addition
■ ...Brij's addition after dd water's dilution
△ ...Brij's dilution after Brij's 56's addition 1 ...Salmonella typhosa      4 ...E.coli 0111:B4 (B Co.)  7 ...E.coli 0113 EC-5
2 ...Salmonella enteritidis  5 ...E.coli 0111:B4 (C Co.)  8 ...Salmonella minnesota (Rc)
3 ...E.coli 0111:B4 (A Co.)  6 ...E.coli UKT-B            9 ...Salmonella minnesota (Re)

1 ...Salmonella typhosa      4 ...E.coli 0111:B4 (B Co.)  7 ...E.coli 0113 EC-5
2 ...Salmonella enteritidis  5 ...E.coli 0111:B4 (C Co.)  8 ...Salmonella minnesota (Rc)
3 ...E.coli 0111:B4 (A Co.)  6 ...E.coli UKT-B            9 ...Salmonella minnesota (Re)

1 ...Salmonella typhosa   4 ...E.coli 0111:B4 (B Co.)   7 ...E.coli 0113 EC-5
2 ...Salmonella enteritidis   5 ...E.coli 0111:B4 (C Co.)   8 ...Salmonella minnesota (Rc)
3 ...E.coli 0111:B4 (A Co.)   6 ...E.coli UKT-B   9 ...Salmonella minnesota (Re)

1 ...Salmonella typhosa   4 ...E.coli 0111:B4 (B Co.)   7 ...E.coli 0113 EC-5
2 ...Salmonella enteritidis   5 ...E.coli 0111:B4 (C Co.)   8 ...Salmonella minnesota (Rc)
3 ...E.coli 0111:B4 (A Co.)   6 ...E.coli UKT-B   9 ...Salmonella minnesota (Re)

LIMULUS REACTION-ACTIVATING SUBSTANCE, METHOD FOR INACTIVATING THE SUBSTANCE AND MEASURING ITS AMOUNT, AND METHOD FOR MEASURING LIMULUS REACTION

BACKGROUND OF THE INVENTION

1. Field of the Invention

The present invention relates to a limulus reaction for activating an amebocyte lysate, which is a hematocyte component of a horseshoe crab (Limulus) and is used for detecting endotoxin or (1→3)-β-D-glucan, and, more particularly, to an endotoxin-specific limulus reaction. More specifically, the present invention relates to a technical field related to (1) a non-endotoxin-like substance that reacts with and activates factor C, which is the first factor of the limulus reaction starting with the endotoxin; (2) means for eliminating the influence of the non-endotoxin-like substance in the limulus reaction; (3) means for measuring the amount of the endotoxin through use of the means for eliminating the influence; and (4) means for measuring the amount of the non-endotoxin-like substance by means of the limulus reaction.

The influence of the non-endotoxin-like substance particularly poses a problem for the measurement of the amount of endotoxin by means of the limulus reaction. Therefore, the present invention further relates to (5) means for measuring the true amount of endotoxin contained in a biological product.

2. Description of the Related Art

Endotoxin is a lipopolysaccharide present in the outer membrane of cell wall of a Gram-negative bacteria and is known to be a highly-pyrogenic substance. Even a trace amount of endotoxin is known to induce various types of morbidity attributable to bacterial infection, as well as fever; e.g., the release of inflammatory cytokines, such as TNF or interleukin-1 (IL-1), in association with the activation of macrophages or endotoxin shock. For these reasons, it is important to detect endotoxin contained in parenteral drugs, and an endotoxin test method is described in Pharmacopoeias in Japan and the U.S., as well as in the Minimum Requirements for Biological Products. Endotoxin is considered to be primarily responsible for the shock induced by Gram-negative infectious diseases. The amount of endotoxin contained in plasma is measured for the purposes of diagnosing Gram-negative infectious diseases, determining treatment effects or prognosis, or early diagnosis of endotoxin shock.

A limulus test method, or an endotoxin test method, is a method of detecting endotoxin by means of activation of an amebocyte lysate of a horseshoe crab performed by Gram-negative bacterial endotoxin (this reaction is called a limulus reaction, reagents using the limulus reaction are called limulus reagents, and assay using the limulus reaction is called limulus assay). At present, this limulus test is roughly classified into a gelation method, turbidimetry which uses as an indicator variations in the degree of turbidity of a gel, and colorimetry which uses as an indicator a color developed as a result of the hydrolysis of a synthetic chromogenic substrate.

In 1978, the U.S. Food and Drug Administration approved the limulus test as an alternative to a rabbit pyrogen test, because of a high degree of correlation between these tests. As a result, the limulus test has been widely applied to a test for the safety of medical devices or drugs which include biological products such as vaccines or blood products. Even in Japan, the limulus test is included, as an alternative to a rabbit pyrogen test, in Japanese pharmacopoeia and the Minimum Requirements for Biological Products.

As shown in FIG. 1, the amebocyte lysate of a horseshoe crab (hereinafter simply referred to as a lysate) contained in the limulus reagent has two coagulation cascades, i.e., A coagulation cascade in which factor C participates by reacting with an endotoxin to become active; and A coagulation cascade in which factor G participates by reacting with (1→3)-β-D-glucan (hereinafter may be referred to as β-D-glucan) to become active. A method of specifically measuring the amount of endotoxin by use of only the former cascade and a method of specifically measuring the amount of β-D-glucan by use of only the latter cascade have already been known (Obayashi T. et. al., Clin. Chem. Acta. 149, pp. 55–65 (1985); endotoxin-specific measurement methods disclosed in WO90/02951, U.S. Pat. No. 5,155,032, U.S. Pat. No. 5,179,006, WO92/03736, WO92/06381, Japanese Patent Laid-Open (kokai) No. 6-258326, Japanese Patent Publication (kokoku) No. 2-18080; β-D-glucan-specific measurement methods disclosed in WO91/19981, WO92/16651). Further, limulus reagents used for specifically measuring the amount of endotoxin and the β-D-glucan, respectively, are already commercially available.

Since there are many cases where the β-D-glucan is mixed in a sample to be subjected to a limulus test, the Japanese Minimum Requirements for Biological Products specify the use of endotoxin-specific limulus reagents.

The endotoxin-specific limulus reagent is also known to react with several substances other than endotoxin, depending on the content of a sample for limulus assay (which signifies a sample to be subjected to measurement which utilizes a limulus reaction). More specifically, like serine proteases such as trypsin, thrombin, factor Xa (the limulus reaction utilizes the reaction of serine-protease contained in the lysate; the action of the above-mentioned serine proteases is similar to that of coagulation enzymes included in the lysate, thereby testing positive) or chymotrypsin (which activates factor C under the absence of endotoxin, thereby testing positive), there are known substances other than endotoxin which specifically react with the endotoxin-specific limulus reagent (the substance will be hereinafter referred to as endotoxin-specific limulus reaction false-positive substances).

There is a known method of eliminating the limulus reaction false-positive substances without deteriorating the activity of endotoxin, which method is to be employed in the measurement of the amount of endotoxin contained in a sample for limulus assay which includes these substances, i.e., in a blood sample (whole blood, plasma, and serum).

For example, there is disclosed means which eliminates the effect of false-positive substances contained in a sample for limulus assay by diluting the sample with a surfactant-containing aqueous solution on the basis of the assumption that the sample is subjected to heat treatment (see Japanese Patent Laid-Open (kokai) No. 6-118086).

Other known methods include means which eliminates the effect of limulus reaction false-positive substances contained in a sample for limulus assay by treating the sample with acid such as perchloric acid (see Japanese Patent Publication (kokoku) No. 63-55671) and means which eliminates the effect of a limulus-reaction inhibition factor contained in the sample by treating the sample with hexadimethrines, such as polybrene, and alkali metal hydroxides (Japanese Patent Laid-Open (kokai) No. 6-70796).

Primarily in the field of biological products, a phenomenon has recently been observed in which drugs that test positive during the endotoxin-specific limulus reaction in spite of the fact that they do not exhibit pyrogenic properties when subjected to a rabbit pyrogen test specified by the Japanese pharmacopoeia. Thus, the use of an endotoxin test method (i.e., endotoxin-specific limulus reaction) described in the Minimum Requirements for Biological Products was found to involve the risk of inadequate evaluation of the safety of drugs.

By the analysis of this phenomenon, the present inventors discovered that the substances which falsely test positive during the endotoxin-specific limulus reaction are different from the conventionally-known limulus reaction-activating substances and are difficult to eliminate by means of any one of the foregoing means for eliminating limulus reaction false-positive substance.

This finding has made it considerably important to provide a method for eliminating the influence on the limulus reaction of the limulus reaction false-positive substances mixed in the biological products and for enabling accurate measurement of only endotoxin.

SUMMARY OF THE INVENTION

Accordingly, a primary object of the present invention is to provide means for specifying and isolating new substances predominantly contained in biological products which indicate falsely positive during the endotoxin-specific limulus reaction and for eliminating the influence of these substances on a limulus reaction, and another object of the invention is to provide a method of measuring the amount of these substances.

As a result of their enthusiastic study of these new substances and the means for eliminating them, the present inventors have established means for isolating these substances and have discovered the remarkable fact that the effect of the substances on the limulus reaction can be eliminated by copresence of a sample for limulus assay with a surfactant or a combination of a surfactant and an alkylamine under non-heating conditions (a specific temperature range of the conditions will be described herein later).

More specifically, the present invention provides:

(1) a limulus reaction-activating substance (which will be described in detail later) which is manufactured by a specific method and possesses specific properties;

(2) the copresence of a sample for limulus assay with a surfactant at a temperature ranging from that higher than a freezing point of the surfactant to 50° C., and the use of a surfactant for inactivating the limulus reaction-activating substance mentioned in (1) above, more preferably, the use of the surfactant which coexists with an alkylamine;

(3) an agent which contains a surfactant for inactivating the limulus reaction-activating substance mentioned in (1) above, a limulus reagent containing the inactivating agent, and a kit for limulus assay which contains the inactivating agent;

(4) a sample for limulus assay in which the limulus reaction-activating substance mentioned in (1) above is inactivated by the surfactant;

(5) a method of measuring endotoxin, which comprises specific processes; and (6) a method of measuring the limulus reaction-activating substance mentioned in (1) above, which comprises specific processes.

DESCRIPTION OF THE PREFERRED EMBODIMENTS

Modes for carrying out the present invention will be described hereinbelow.

A. MEANS FOR SPECIFYING AND ISOLATING LIMULUS REACTION-ACTIVATING SUBSTANCE OF THE PRESENT INVENTION

A limulus reaction-activating substance of the present invention (hereinafter also referred to as a limulus reaction-activating substance) is a new substance which indicates falsely positive during an endotoxin-specific limulus reaction. This substance is specified and isolated by means of the following procedure.

A sample for limulus assay [which is predominantly a biological product (e.g., blood products, vaccines, antibiotics which will be described later)] can be purified by means of various isolation means which utilize physical and chemical properties of the limulus reaction-activating substance. For example, the isolation means comprises processing of the sample through use of an ordinary protein precipitant, ultrafiltration, gel filtration, centrifugation, electrophoresis, gel permeation chromatography, ion exchange chromatography, affinity chromatography, reversed phase chromatography, hydrophobic chromatography, or dialysis. As a matter of course, these isolation means may be employed in combination, as required.

Of these isolation means, the gel permeation chromatography is preferred, with gel permeation chromatography which employs high-performance liquid chromatography being more preferred.

More specifically, the sample is applied to a chromatography column and is eluted with distilled water which serves as a solvent and is free of endotoxin and $\beta$-D-glucan. The flow rate of the solvent is not limited to any particular rate, but a flow rate of 0.5 ml/min. or thereabouts is preferred.

An aqueous solution of polymyxin B sulfate is added to eluted fractions in such a way that the final concentration of polymyxin B sulfate reaches 0.5 mg/ml, thereby completely inhibiting the endotoxin activity. The fractions are measured by means of an endotoxin-specific limulus reagent and positive fractions are collected, whereby the limulus reaction-activating substance can be obtained.

The thus-manufactured limulus reaction-activating substance is predominantly present in biological products, such as vaccines or albumin products, and has the following characteristics. The characteristics of the substance will be described in the embodiment section hereinbelow.

Figure 8A:
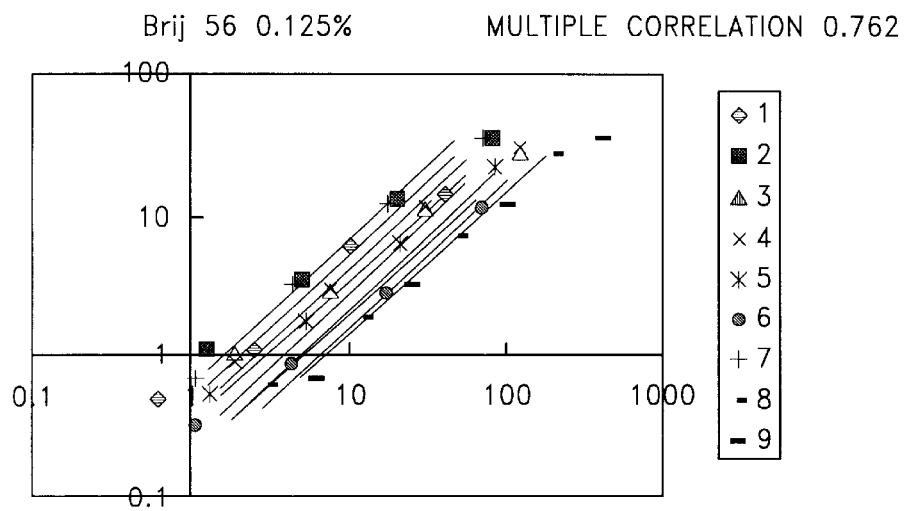
FIGS. 8A and 8B show the effect of a surfactant and triethylamine on various endotoxin response (in a biological product)
Figure 8B:
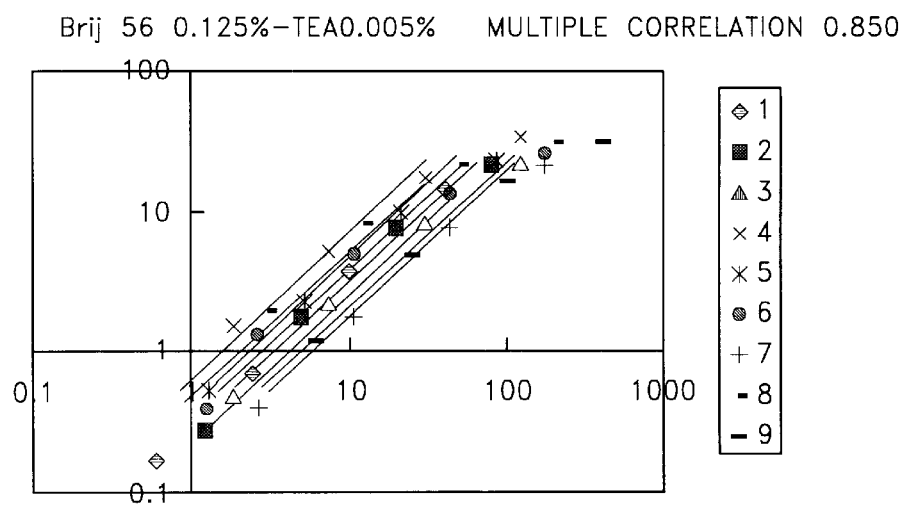
Figure 9:
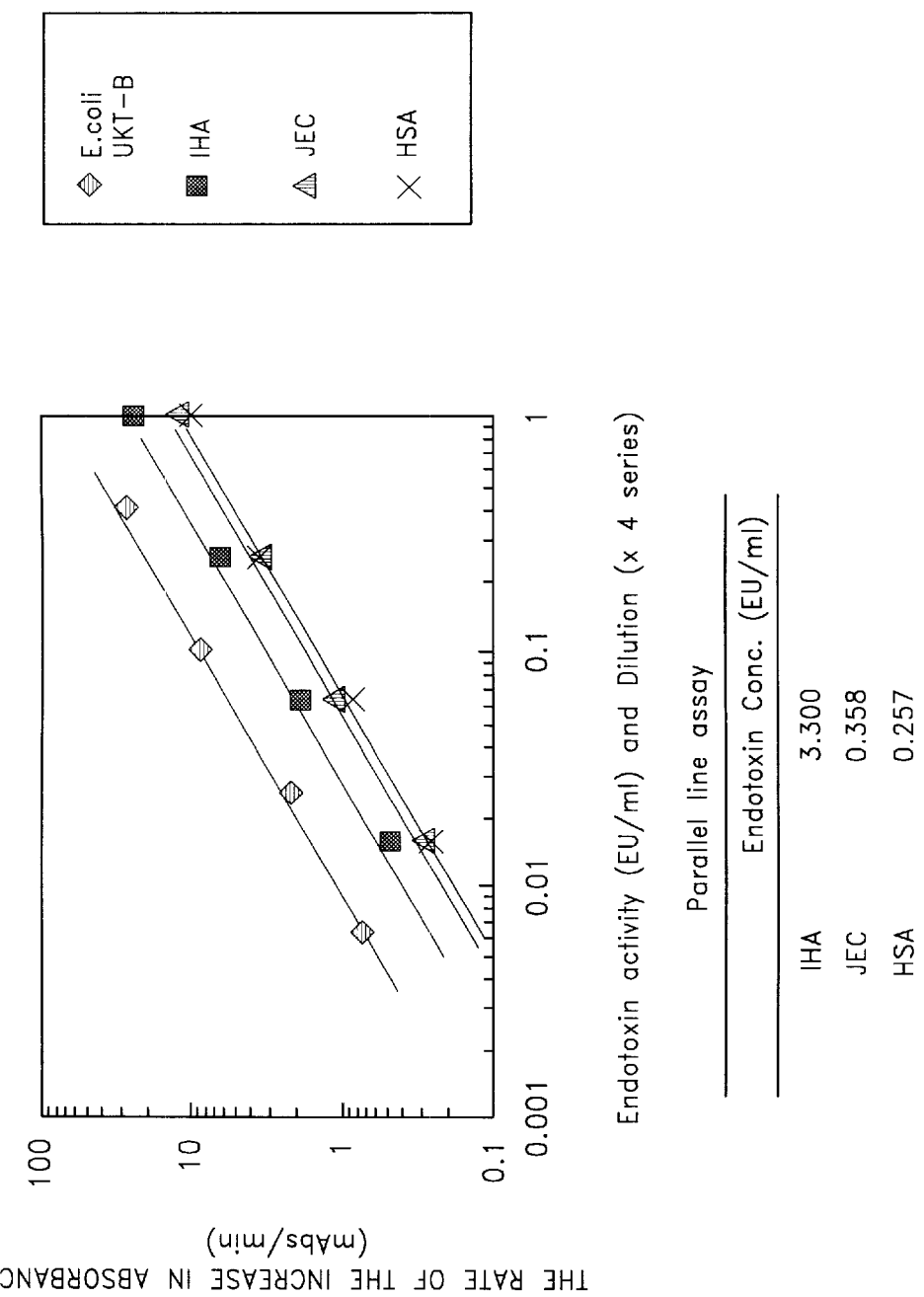
FIG. 9 is a plot showing the measurement of the amount of endotoxin contained in a biological product by means of quantitative assay on parallel regression line.

FIGS. 8A and 8B show the effect of a surfactant and triethylamine on various endotoxin responses (in a biological product); and FIG. 9 is a plot showing the measurement of the amount of endotoxin contained in a biological product by means of quantitative assay on parallel regression line.

The isolated limulus reaction-activating substance has the following characteristics:

(1) exhibiting limulus reaction activity;
(2) reactive with an endotoxin-specific limulus reagent;
(3) activating factor C of an amebocyte lysate of a horseshoe crab;
(4) exhibiting no pyrogenicity by a rabbit pyrogen test;
(5) exhibiting no endotoxic activity;
(6) exhibiting no (1→3)-β-D-glucan activity;
(7) exhibiting no serine protease activity;
(8) maintaining the limulus reaction activity when coexisting with polymyxin B;
(9) maintaining the limulus reaction activity when coexisting with colistin;
(10) maintaining the limulus reaction activity when being exposed to 0.2M hydrochloric acid at 37° C. for 60 min;
(11) maintaining the limulus reaction activity when being exposed to 0.2M potassium hydroxide at 37° C. for 60 min;
(12) reducing the limulus reaction activity when being exposed to polyoxyethylene hexadecylether. The above substance is reported to increase the toxicity of endotoxin such as that reported with regard to TSST-1 of staphylococcal exotoxin (Staphylococcal toxic shock syndrome toxin-1) [H. Fujikawa et. al., Infect Immun., 52, 134 (1986)], or to have a physiological action or toxicity analogous to that of endotoxin, for example, the production of inflammatory mediator. Accordingly, elucidating the action of the limulus reaction-activating substance isolated for the first time by the present invention in an organism or in various types of morbidity is of considerable importance. Further, a method of measuring the limulus reaction-activating substance of the present invention provides considerably important information, as does the method of measuring endotoxin.

The present inventors have observed that the limulus reaction-activating substance is present predominantly in biological products and is contained in comparatively large amounts in biological products imported from overseas. The origin of this substance is not clear, and the possibility of biological products being contaminated with the substance during the course of manufacture of the products cannot be denied. It is expected that the method of measuring the amount of the limulus reaction-activating substance of the present invention will be applied to determining the contamination of biological products with the substance in manufacturing processes or to check final products. As a result, the production of biological products which are much safer than existing biological products is anticipated. The method of measuring the limulus reaction-activating substance of the present invention will be described later.

B. MEANS FOR INACTIVATING THE LIMULUS REACTION-ACTIVATING SUBSTANCE (hereinafter also referred to as a method of inactivating the limulus reaction-activating substance)

In a case where the limulus reaction-activating substance is contained in a sample for limulus assay, the substance indicates falsely positive in response to the limulus reagent, thereby reducing the accuracy of detection of a desired substance (e.g., endotoxin).

Specifically, the means for inactivating the limulus reaction-activating substance of the present invention may be a method of mixing the substance with a surfactant at a temperature ranging from that higher than a freezing point of the surfactant to 50° C.

The surfactant used for the present invention is not limited to any particular surfactant, so long as it does not impair the limulus reaction of endotoxin as a result of dissociation of the endotoxin micelles, does not activate a limulus reaction, or does not inhibit active serine proteases. The surfactant may be selected from a group comprising cationic surfactants, anionic surfactants, ampholytic surfactants, nonionic surfactants, and natural surfactants. It is preferred to select the nonionic surfactants which less directly act on endotoxin. Further, these surfactants may be used in combination, as required.

Of the nonionic surfactants, a surfactant having polyoxyethylene in a hydrophilic moiety thereof (hereinafter also referred to as polyoxyethylenes) is preferred. Examples of the polyoxyethylenes include polyoxyethylene alkyl ether (represented by $C_n2_{n+1}(OCH_2CH_2)_xOH$ or usually abbreviated as $C_nE_x$), polyoxyethylene alkylphenyl ether ($C_n\Phi E_x$) having a phenyl group between an alkyl chain and a polyoxyethylene chain, and acylpolyoxyethylene sorbitan ($C_n$-sorbitan-$E_x$).

These surfactants are respectively known by common names (or tradenames), such as Brij (CnEx), Triton X (Cn(Ex), and Tween (Cn-sorbitan-Ex), and are widely used for the purpose of solubilizing membrane protein.

Although the polyoxyethylene chain of the polyoxyethylenes used in the present invention [i.e., $(OCH_2CH_2)_xOH$ of the foregoing formula, also abbreviated as "Ex"] is not particularly limited, polyoxyethylenes (where x=an integer from 2 to 25 inclusive, preferably x=an integer from 4 to 23 inclusive, and more preferably x=an integer from 7 to 13 inclusive) are preferred. Although the number of carbons of the alkyl group (i.e., $C_nH_{2n+1}$ of the formula, which is also abbreviated as "$C_n$") of the polyoxyethylenes employed in the present invention is not particularly limited, it is preferred for polyoxyethylenes to have an n=an integer from 8 to 18 inclusive.

Examples of the polyoxyethylenes include polyoxyethylene dodecyl ether, polyoxyethylene hexadecyl ether (also referred to as polyoxyethylene cetyl ether), polyoxyethylene isooctylphenyl ether, polyoxyethylene nonylphenyl ether, polyoxyethylene fatty acid ester, and polyoxyethylene sorbitol ester.

Of these compounds, polyoxyethylene hexadecyl ether is very preferred.

It is preferred that these surfactants be used as aqueous solution and have a certain micelle size.

The solvent of the aqueous solution of the surfactant may be a buffer solution. Preferably, the pH of the buffer solution is adjusted to be in the range of optimum pH of the cascade participated with factor C (more preferably a pH of about 7 to 9). Examples of the buffer solution include Good's buffers [e.g., HEPES (N-2-hydroxyethylpiperazine-N'-2-ethanesulfonic acid buffer), colaminechloride buffer, BES buffer, MOPS buffer, TES buffer, HEPPS buffer (N-2-hydroxyethylpiperazine-N'-3-propanesulfonic acid buffer), Tricine buffer, glycinamide buffer, or Bicine buffer, TAPS buffer]; tris-hydrochloric acid buffer; or the like.

The amount of a surfactant to coexist with the limulus reaction-activating substance is not particularly limited and can be changed depending on the amount of limulus reaction-activating substance or the type and amount of surfactant to coexist with the substance, as required. For example, specific concentrations of surfactant are usually set to 0.005% to 0.8% (weight by volume), preferably 0.01% to 0.5% (weight by volume), and more preferably 0.05% to 0.3% (weight by volume) as the final concentration of the surfactant when it comes into contact with the sample. However, these concentrations are merely illustrative and are not intended to be construed in a limiting sense.

An aqueous solution of a desired surfactant can be prepared by subjecting the solution to means for removing endotoxin from the solution, e.g., an activated carbon treatment, a membrane filtering treatment, or an autoclave treatment.

The method and the sequence of causing the surfactant or the aqueous solution of a surfactant to coexist with the sample containing the limulus reaction-activating substance are not particularly limited, so long as the surfactant coexists in predetermined concentrations with the sample without being subjected to modification or disruption. The objective of the present invention can be achieved even if a surfactant is added to a limulus reagent in advance and the limulus reagent is mixed and concurrently reacted with a sample. However, in terms of effect, it is preferred to mix a surfactant with the sample before limulus reaction. The aqueous solution of the surfactant is desirably mixed with the sample at a ratio of 0.1 to 10:1 parts by volume. However, the ratio is not particularly limited, so long as the surfactant is added in a predetermined concentration into the sample and the effective concentration is maintained.

In order to inactivate the limulus reaction-activating substance, the surfactant must be mixed with the substance at a temperature ranging from that higher than a freezing point of the surfactant to 50° C. At a temperature below the freezing point of the surfactant, the surfactant becomes frozen, thereby making it difficult to smoothly perform desired inactivation of the substance. In contrast, if the temperature exceeds 50° C., endotoxin or the other substances to be measured is also inactivated, thereby making it difficult to correctly measure the amount of endotoxin or the like.

The limulus reaction-activating substance can be brought into contact with the surfactant preferably at a temperature ranging from 1° C. to 50° C., more preferably at a temperature ranging from 4° C. to 50° C., even more preferably at a temperature ranging from 4° C. to 45° C., and particularly preferably at a temperature ranging from 15° C. to 40° C.

In this respect, the present invention greatly differs from the existing technique (as disclosed in Japanese Patent Laid-Open (kokai) No. 6-118086) which employs a surfactant and actively heats to inactivate a limulus reaction false-positive substance.

The method for achieving copresence of the sample and the surfactant is not particularly limited. The sample and the surfactant are usually made to coexist with each other by adding them together and sufficiently mixing this mixture.

There is no particular limitation on the time period over which the sample coexists with the surfactant at a temperature ranging from that higher than a freezing point of the surfactant to 50° C., so long as the endotoxin molecules and micelles associated with them are physically and chemically stable and are not adsorbed to a container. The time period is usually set to a period ranging from several seconds to five minutes, and one to two minutes are adequate for the time period. Thus, the limulus reaction-activating substance can be inactivated through use of the surfactant within a very short period of time.

The foregoing method of inactivating the limulus reaction-activating substance can be directly applied to the inactivation of the limulus reaction-activating substance contained in the sample for limulus assay.

The present invention comprises the use of a surfactant for the purpose of inactivating the limulus reaction-activating substance so as to mix the sample with the surfactant at a temperature ranging from that higher than a freezing point of the surfactant to 50° C. As will be described later, an alkylamine preferably coexists with the sample in addition to surfactant. The present invention comprises the use of a surfactant for the purpose of inactivating the limulus reaction-activating substance so as to mix the sample with the surfactant and an alkylamine at a temperature ranging from that higher than a freezing point of the surfactant to 50° C.

As described above, the present invention provides the methods for inactivating the limulus reaction-activating substance, thereby directly yielding a sample for limulus assay which contains the limulus reaction-activating substance inactivated by the surfactant. This inactivation methods can be applied to various forms.

For example, the inactivation methods can be applied to a surfactant-contained agent for inactivating a limulus reaction-activating substance based on the copresence of the sample and the surfactant at a temperature ranging from that higher than a freezing point of the surfactant to 50° C.

The inactivation methods can be also applied to a limulus reagent which contains the inactivation agent, a kit for limulus assay which contains the limulus reagent, or a kit for limulus assay which contains both the inactivation agent and the limulus reagent.

The term "limulus assay" used herein signifies measurement which uses a limulus reaction. The term "kit for limulus assay" used herein signifies a kit which is used for assay which uses a limulus reaction and contains at least a limulus reagent.

In addition to the limulus reagent, the kit can contain an optional reagent, as required. For example, this reagent includes distilled water for blank test purposes or reactive-reagent-dissolution/reaction buffer solutions. However, the reagent is not limited to these examples.

The present invention provides an agent which contains a surfactant and inactivates the limulus reaction-activating substance, a limulus reagent containing the inactivating agent, and a kit for limulus assay which contains the limulus reagent and the inactivating agent. Preferably, the limulus reagent is an endotoxin-specific limulus reagent.

The present invention further comprises a method of eliminating the effect of a sample for limulus assay on the limulus reaction, which method is characterized by copresence of a sample for limulus assay and a surfactant at a temperature ranging from that higher than a freezing point of the surfactant to 50° C. to inactivate the limulus reaction-activating substance.

The present invention includes a sample for limulus assay which contains the limulus reaction-activating substance inactivated by the surfactant in the previously-described manner.

The sample to be subjected to the inactivation of the limulus reaction-activating substance is not particularly limited, so long as the sample is subjected to the detection of endotoxin by means of a limulus reaction. Particularly preferable samples are so-called biological products which are biologically-derived limulus samples and have a higher possibility that the limulus reaction-activating substance is contained.

The term "biological products" used herein is a concept which excludes blood fractions containing whole blood; i.e., whole blood, plasma, serum, or the like, which is not biologically processed. More specifically, the biological products are biologically-processed products including vaccine preparations [which are generally prepared for the purpose of reducing a morbidity rate by increasing a blood antibody titer with respect to a target virus by means of vaccination; for example, vaccine preparations include inactivated vaccines which are usually manufactured by proliferating virions in a host, such as a transovarian allantoic cavity or a brain, and decomposing and inactivating highly-purified virions {e.g., influenza vaccine (influenza HA vaccine), Japanese Encephalitis vaccine, or the like} or attenuated vaccine], biologically-processed blood products [e.g., human serum albumin or human plasma protein which is usually produced from a starting material, such as plasma, and are fractionated and prepared to a high purity by changing various conditions of the starting material, such as pH, ionic strength, or ethanol concentrations and using a fractional precipitation method (e.g., Cohn fractionation) on the basis of the degree of dissolution of protein], or antibiotics.

The vaccine takes the form of a colorless-and-transparent or slightly-opaque, odorless liquid article to which a stabilizing agent such as gelatin has been added. There is also freeze-dried vaccine which is a slightly-yellowish-white powdery solid. This vaccine is used in liquid form prepared by adding a specified quantity of distilled water is added to the solid.

C. MEANS FOR MEASURING THE AMOUNT OF ENDOTOXIN WHICH USES THE MEANS FOR INACTIVATING THE LIMULUS REACTION-ACTIVATING SUBSTANCE
(hereinafter also referred to as an endotoxin measurement method)

By virtue of the use of the foregoing means for inactivating the limulus reaction-activating substance, there is provided a method of measuring the amount of endotoxin contained in a sample for limulus assay, comprising:

(1) a first step of mixing the sample with a surfactant at a temperature ranging from that higher than a freezing point of the surfactant to 50° C. to thereby inactivate the limulus reaction-activating substance contained in the sample; and (2) a second step of subjecting the sample whose limulus reaction-activating substance is inactivated in the first step to a limulus reagent and of measuring a change through a limulus reaction.

Preferably, the sample, the surfactant, and the alkylamine are brought into copresence with each other at a temperature ranging from that higher than a freezing point of the surfactant to 50° C. The technical significance of the addition of an alkylamine will be described later.

Desirably, the sample is a biological product, and the preferred biological products have already been described.

The amount of endotoxin contained in the sample can be more easily measured by use of a limulus reagent which contains an agent containing a surfactant for inactivating the limulus reaction-activating substance.

Therefore, there is further provided a method of measuring the amount of endotoxin contained in a sample for limulus assay, comprising:

(1) a first step of preparing a limulus reagent which contains an agent for inactivating the limulus reaction-activating substance, and (2) a second step of subjecting the sample to a limulus reaction through use of the limulus reagent prepared in the first step.

In the present invention, an endotoxin-specific limulus reagent is preferably used, although usable limulus reagents are not particularly limited, so long as the reagents enable the detection of endotoxin, in view that the limulus reaction-activating substance falsely tests positive during the course of the detection of endotoxin.

If the sample clearly does not contain any β-D-glucan, use of the endotoxin-specific limulus reagent is not necessarily required. In this case, a limulus reagent which detects both endotoxin and β-D-glucan may also be used.

The limulus reagent is not limited, so long as the reagent enables the detection of endotoxin. In addition to a limulus reagent utilizing synthetic substrate method (end-point assay or kinetic assay), a limulus reagent utilizing an ordinary gelation method or turbidimetry (end-point assay or kinetic assay) may be employed. In the present invention, various limulus reagents commercially available can be used; e.g., Toxicolor System LS-6, Toxicolor System LS-20, Toxicolor System LS-200, Endospecy ES-6, Endospecy-ES-200, Pyrodick, Pregel, Pregel-S, Pregel-M, Pyrotell Multitest, Pyrotell Single Test, Pyrotell-T (all of which are available from Seikagaku Corporation); Limulus J Test Wako, Limulus HS-J Test Wako, Limulus J Single Test Wako, Limulus HS-J Single Test Wako, Limulus F Test Wako, Limulus HS-F Test Wako, Limulus F Single Test Wako, Limulus HS-F Single Test Wako, Limulus ES-II Test Wako, Limulus ES-II Single Test Wako, Limulus ES-III Test Wako, Limulus ES-J Test Wako (all of which are available from Wako Pure Chemical Industries); Pyrogent, Pyrogent Multitest, Pyrogent Single Test, QCL-1000, Kinetic QCL System (all of which are manufactured by Bio-Whitecker Co., Ltd and are available from Daiichi Kagaku Yakuhin Co., Ltd.); Co-Test Endotoxin (available from Chromogenic AB Ltd.); Endochrome, Endochrome-K (which is manufactured by Charles River Laboratory and is available from End Safe Ltd.); Pyrosate (available from Hemachem Ltd.); or Pyrochrome (available from Capecod Ltd.).

Of these commercially-available limulus reagents, two types of reagents, i.e., Endospecy and Limulus ES Test, are specific to endotoxin. The limulus reagent to be used in the present invention is not limited to the aforementioned commercially-available limulus reagents. So long as a series of enzymes of factor C pathway (i.e., a coagulation pathway) are activated as a result of reaction with endotoxin, it is also possible to use a lysate which is prepared by means of a known method from the hematocyte of a horseshoe crab belonging to; e.g., the genera *Tachypleus tridentatus*, *Tachypleus gigas*, or *Tachypleus rotundicauda* (of Asia) or the genus *Limulus polyphemus* (of North America.

More specifically, a lysate can be produced from a hemolymph of the horseshoe crab by means of a method disclosed in, e.g., J. Biochem., 80, pp. 1011 to 1021 (1976).

The endotoxin-specific limulus reagent can be prepared by specifically inhibiting, adsorbing, or eliminating factor G of the lysate (e.g., WO 90/02951, U.S. Pat. No. 5,155,032, U.S. Pat. No. 5,179,006, WO 92/03736, WO 92/06381, or Japanese Patent Application No. 5-61464) or by fractionating and reconstituting factor-C-based components [e.g., Japanese Patent Publication (kokoku) No. 2-18080, or Obayashi T. et. al., Clin. Chem. Acta., 149, pp. 55 to 65 (1985)].

The endotoxin-specific limulus reagent can also be produced from factor C, a synthetic peptide substrate which will be described later, a buffer solution and bivalent metal salt, or factor C, factor B, the synthetic peptide substrate, a buffer solution and a bivalent metal salt.

Examples of the synthetic peptide substrate include synthetic peptide substrates whose carboxyl group of arginine at C-terminal of peptide capable of becoming a substrate of active factor C (e.g., peptide whose E-terminal is protected and which has an arrangement such as Val-Pro-Arg, Leu-Gly-Arg, or Ile-Glu-Ala-Arg or e.g., methoxycarbonyl-D-hexahydrotylosil-Gly-Arg) is combined through amide bonding with chromogenic residues [e.g., p-nitroaniline, p-(N, N-diethylamino)aniline, p-(N-ethyl-N-(hydroxyethyl) aniline], fluorescent residues (e.g., 7-aminomethylcoumarin), luminous residues, or ammonia.

When the measurement of the amount of endotoxin is carried out by using such a produced endotoxin-specific limulus reagent, the activity of amidase can be determined by measurement of a reaction product (e.g., p-nitroaniline or ammonia) which is produced as a result of active factor C acting on the synthetic substrate. According to an example of the measurement method used for measuring the amount of endotoxin, a mixture comprising a liquid to be tested and factor C, a buffer liquid and bivalent metal salt is prepared and reacted with a synthetic substance, and, if necessary, the product is transformed into another pigment.

Subsequently, the pigments, fluorescent substances, luminous substances, or ammonia resulting from the reaction are measured by a spectrophotometer [see Japanese Patent Publication (kokoku) Nos. 63-26871 and 3-66319], a fluorophotometer, a chemoluminescense measuring device, or an ammonia detection electrode (see Japanese Patent Laid-Open (kokai) No. 62-148860), respectively.

The inventors have discovered that the coexistance of alkylamine with a surfactant in the detection system of endotoxin, enables endotoxin to be maintained in a suitable associated or dispersed state and minimizes the difference in solubility or reactivity between endotoxin owing to the type of bacterium, thereby providing reproducible data. In short, it is preferred that an alkylamine be brought into copresence with the sample and the surfactant when the sample and the surfactant coexist with each other at a temperature ranging from that higher than a freezing point of the surfactant to 50° C.

Although the method of bringing the sample, the surfactant, and an alkylamine into copresence is not particularly limited, it is preferred to employ a method in which after an alkylamine and a surfactant have been mixed to a predetermined concentration in advance, and the thus-produced mixture is directly mixed with a sample for limulus assay. If an alkylamine is maintained at a predetermined concentration with respect to the sample, any method may be employed, e.g., a method of bringing a surfactant into copresence with the sample and an alkylamine after the alkylamine has been brought into copresence with the sample, a method of bringing an alkylamine into copresence with the sample and the surfactant after the surfactant has been brought into copresence with the sample, or a method of bringing an alkylamine into copresence with a limulus reagent in advance.

For example, the effect of an alkylamine can be readily achieved by the sole addition of an alkylamine to the aqueous solution of surfactant prepared to a predetermined concentration in such a way that the final concentration of the alkylamine reaches the range of 0.0001% to 0.05% (weight by volume), and more preferably the range of 0.002% to 0.01% (weight by volume), when the alkylamine comes into contact with the sample for limulus assay, thereby resulting in a further improvement in the advantageous results of the present invention.

If the amount of the alkylamine contained in the solution is under 0.0001% (weight by volume), a desired effect will be difficult to achieve. In contrast, if the amount of alkylamine exceeds 0.05% (weight by volume), there is no corresponding increase in a resultant effect.

Alkylamine may have a substituent. Any substance can be used as alkylamine, so long as the substance is usually soluble in a polar solvent or water and cannot be readily decomposed. Preferred examples of alkylamines include secondary amines such as methylmethaneamine or ethylethaneamine, and more preferred examples include tertiary amines such as dimethylamine or dimethylethaneamine. More specifically, there may be used N-ethylethaneamine (diethylamine), 2,2'-iminodiethanol, bis(2-hydroxyethyl)amine (diethanolamine), N,N-dimethylmethaneamine (trimethylamine), N,N-diethylethaneamine (triethylamine), or tris(2-hydroxyethyl) amine (triethanolamine).

D. MEANS FOR MEASURING THE AMOUNT OF THE LIMULUS REACTION-ACTIVATING SUBSTANCE (hereinafter also referred to as a method of measuring the limulus reaction-activating substance)

The present invention provides a method of specifically measuring solely endotoxin by inactivating the limulus reaction-activating substance contained in a biological product, i.e., a method of more appropriately testing the safety of drugs. Furthermore, the present invention provides a method of specifically measuring solely the limulus reaction-activating substance. More specifically, the amount of limulus reaction-activating substance is calculated by measuring a total amount of limulus reaction-activating substance and endotoxin (or the amount of substance which reacts with a limulus reagent) through use of an ordinary limulus test, and by subtracting from the thus-measured total amount the amount of endotoxin obtained by various means alone.

In the present invention, it is possible to use one type of a biological product or a mixture of two or more types of biological products.

The present invention also comprises a method in which the endotoxin alone is inactivated through use of a substance which specifically inactivates solely endotoxin in the sample—e.g., acid, alkali, or polymyxins such as polymyxin B or colistin—and by measuring the limulus reaction-activating substance by means of the ordinary limulus test.

Of these endotoxin-inactivating substances, polymyxins such as polymyxin B or colistin may sometimes erroneously reflect a measured value of the limulus reaction-activating substance. In other terms, a substance which inhibits polymyxins from neutralizing endotoxin sometimes coexists in the sample. In contrast, in a case where endotoxin is inactivated through use of acid or alkali, the foregoing problems will not arise. Therefore, acid or alkali can be used as a desirable endotoxin-inactivating substance.

Although the acid used herein is not limited to any particular acid, strong acid such as hydrochloric acid, sulfuric acid, or nitric acid is preferred. Further, although alkali is not limited to any particular alkali, strong alkali such as sodium hydroxide or potassium hydroxide is preferred. The sample is usually treated by the addition of acid or alkali thereto in such a way that the sample coexists with acid or alkali.

Although the concentration of acid or alkali in the sample is not particularly limited, the final concentration of acid or alkali in the sample is preferably set to a value of 0.05M or more, and more particularly to a value ranging from 0.05 to 0.2 M or thereabouts.

Before being subjected to measurement through use of the limulus reagent, an endotoxin-inactivated sample for limulus assay must be neutralized. Preferably, after the neutralization of the sample, the pH of the sample is maintained as a pH ranging from 6 to 9.

More specifically, the present invention is directed to a method of measuring the amount of the limulus reaction-activating substance in a sample for limulus assay comprising:

(1) a first step of measuring the total amount of substances which react with the limulus reagent contained in the sample through the use of the limulus reagent;

(2) a second step of measuring the amount of endotoxin contained in the sample by means of the method of measuring endotoxin; and (3) a third step of calculating the amount of the limulus reaction-activating substance through determining the difference between the total amount of the substances—which react with the limulus reagent—measured in the first step and the amount of endotoxin measured in the second step.

The limulus reagents used in the first and second steps must be of the same type. In a case where an endotoxin-specific limulus reagent is used in the first step, the endotoxin-specific limulus reagent must be used in the second step as well. Limulus reagents which are usable for these steps are the same as those previously described as being usable for the endotoxin measurement method. Endotoxin-specific limulus reagents are preferred.

The present invention also comprises a method of measuring the amount of the limulus reaction-activating substance contained in a sample for limulus assay, the method comprising:

(1) a first step of treating the sample with an endotoxin-inactivating substance, particularly acid or alkali; and (2) a second step of measuring the limulus reaction-activating substance by causing the endotoxin-inactivated sample obtained in the first step to a limulus reagent, and by measuring a change through a limulus reaction.

As previously described, before being subjected to measurement through use of the endotoxin-specific reagent, the endotoxin-inactivated sample obtained in the first step must be maintained.

E. MEANS FOR MEASURING THE TRUE AMOUNT OF ENDOTOXIN CONTAINED IN A BIOLOGICAL PRODUCT (or a method of measuring endotoxin contained in a biological product):

The method of measuring endotoxin contained in a biological product according to the present invention enables the measurement of the true amount of endotoxin contained in a biological product by means of a limulus reaction which is found to be impossible for the existing known method to measure. The present invention also comprises a series of steps of measuring the amount of endotoxin through use of the limulus reagent after having eliminated the effect of the limulus reagent false-positive substance (e.g., the limulus reaction-activating substance) contained in a biological product.

The effect of the limulus reaction false-positive substance contained in a biological product is eliminated by use of a surfactant, whereby a biological product to be subjected to limulus-reagent is brought into copresence with the surfactant at a temperature ranging from that higher than a freezing point of the surfactant to 50° C.

As described hereinabove, it is preferable to mix the biological product with an alkylamine in addition to the surfactant. More specifically, it is particularly preferred to use a surfactant and an alkylamine in such a way that the biological product, the surfactant, and the alkylamine coexist with each other at a temperature ranging from that higher than a freezing point of the surfactant to 50° C.

The present invention also comprises a method of pretreating a biological product to be subjected to limulus-reagent measurement, the method being characterized by copresence of a surfactant with the biological product at a temperature ranging from that higher than a freezing point of the surfactant to 50° C.

The present invention also comprises a biological product to be subjected to limulus-reagent which is obtained by this pretreatment and which contains a surfactant.

As a result of elimination of the influence of the limulus reaction false-positive substance contained in a biological product as described above, there is provided a method of measuring endotoxin contained in the biological product, the method comprising:

(1) a first step of mixing the biological product with a surfactant at a temperature ranging from that higher than a freezing point of the surfactant to 50° C.; and (2) a second step of subjecting the sample for limulus assay obtained in the first step to a limulus reagent, and of measuring a change through a limulus reaction.

More preferably, in the first step, the sample is brought into copresence with a surfactant and an alkylamine at a temperature ranging from that higher than a freezing point of the surfactant to 50° C.

Limulus reagents which are usable for these steps are the same as those previously described as being usable for the endotoxin measurement method. Endotoxin-specific limulus reagents are more preferred.

EXAMPLES

The present invention will be more specifically described hereinbelow with reference to examples which are illustrative but not restrictive.

MANUFACTURE EXAMPLE

Manufacture of a Limulus Reaction-Activating Substance of the Present Invention

Figure 1:
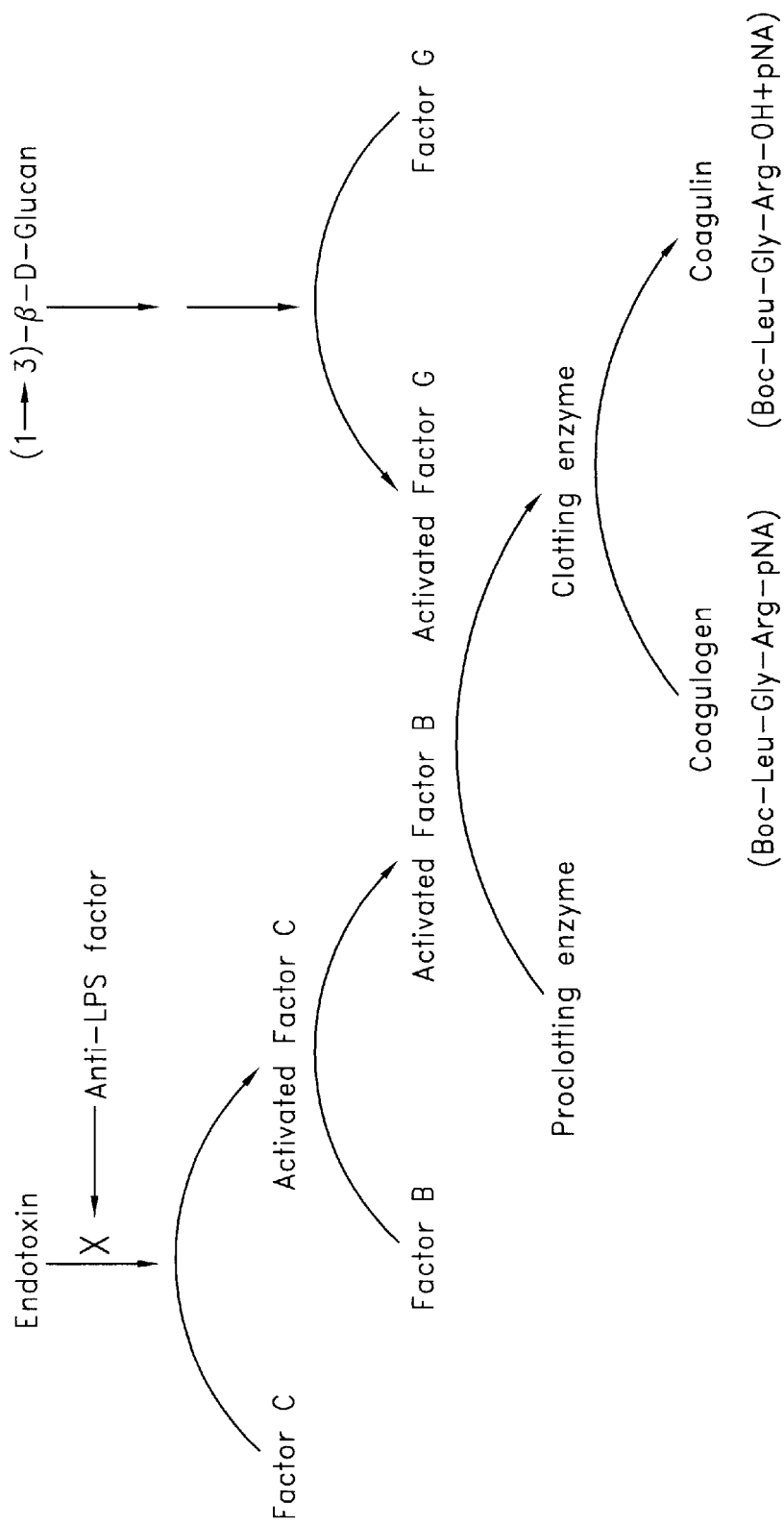
FIG. 1 is a diagram showing two mechanisms for activating the coagulation cascade of a horseshoe crab.
Figure 2:
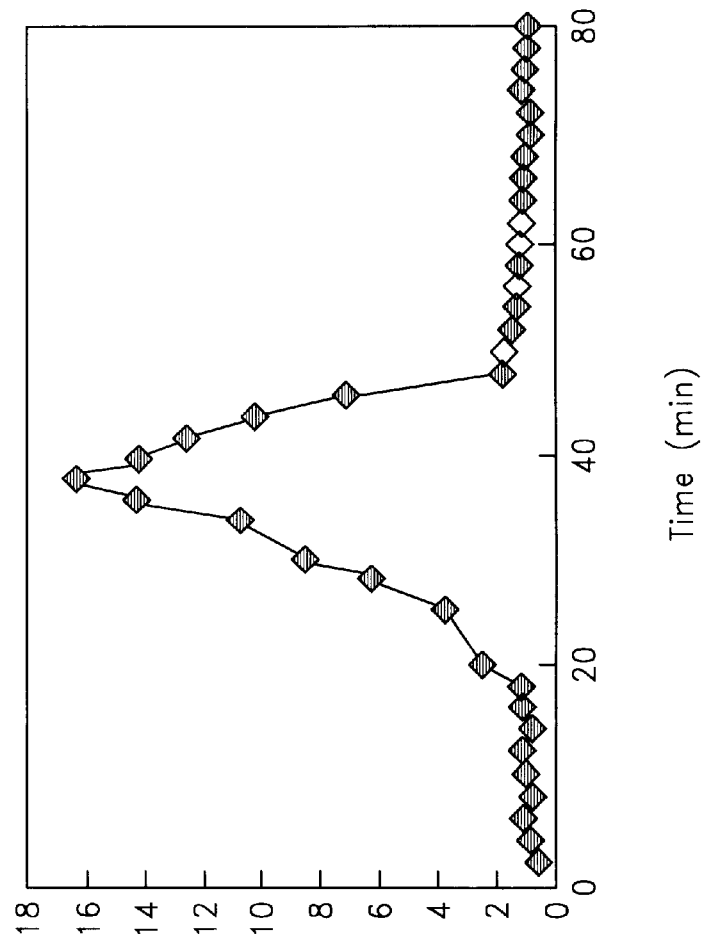
FIG. 2 is an elution pattern of a limulus reaction-activating substance of the present invention contained in an influenza vaccine obtained by means of high-performance liquid chromatography.

50 µl of influenza HA vaccine (IHA-Lot A) and 50 µl of Japanese B encephalitis (JEC-Lot A) were subjected to gel permeation chromatography employing high-performance liquid chromatography, i.e., the vaccines were applied to columns TSKgel G4000SW and TSKgel G3000SW which were joined together (columns manufactured by Toso Co., Ltd, each column measuring 7×30 mm and having a volume of 14.3 cm$^8$). The vaccine was eluted with a solvent, or distilled water from which endotoxin and β-D-glucan had been removed, at a flow rate of 0.5 ml/min. The thus-eluted liquid was fractionated every 1 ml. The pattern of elution of influenza HA vaccine is shown in FIG. 2.

An aqueous solution of polymyxin B sulfate was added to each of the thus-eluted factions in such a way that the final concentration of the fraction reached 0.5 mg/ml, thereby completely inhibiting the activity of endotoxin. Subsequently, limulus reaction was measured through use of Endospecy (which is an endotoxin-specific reagent and available from Seikagaku Corporation), and positive fractions (i.e., active fractions) were collected, whereby a limulus reaction-activating substance was obtained.

EXAMPLE 1

Comparison between a limulus reaction-activating substance mixed in vaccine preparations and endotoxin with regard to physical properties and various characteristics Table 1 shows the results of comparison between the limulus reaction-activating substance manufactured from influenza HA vaccine (IHA-Lot A) and Japanese B encephalitis (JEC-Lot A) in the foregoing example, and various types of purified endotoxin (Westphal type endotoxin prepared from *E. coli* 0111:B4, *E. coli* 055:B5, *E. coli* UKT-B, *Salmonella minnesota* R595, *S. marcescens*, *S. typhimurium*, *S. abrtus* equi.) with regard to physical properties. After having been treated under the conditions provided below Table 1, the samples for limulus assay was made to react with an endotoxin-specific limulus reagent (Endospecy available from Seikagaku Corporation) on a microtiter plate—which was free from endotoxin and (1→3)-β-D-glucan (e.g., Toxipet Plate 96F available from Seikagaku Corporation)—in a microplate reader (Well Reader SK601 available from Seikagaku Corporation) for 30 min. The concentration of endotoxin was automatically calculated from the rate of changes (mAbs/min.) in the absorbance of light [having a wavelength of 405 to 492 nm] per minute. As a result, the residual activity of the limulus reaction-activating substance (%) and of endotoxin was calculated, taking the residual activity of an unprocessed control group as 100%. From Table 1, it is evident that the limulus reaction-activating substance contained in the influenza HA vaccine, the Japanese B encephalitis, or the like, has the effect of directly activating an endotoxin-sensitive factor (i.e., factor C) present in the amebocyte of a horseshoe crab. Further, it is obvious that the limulus reaction-activating substance is a non-serine-protease (incapable of activating factor C, a proclotting enzyme, or directly hydrolyzing a synthetic substrate) and non-(1→3)-β-D-glucan (incapable of activating factor G) molecule and has physical properties similar to those of endotoxin which form a macromolecular amphipathic micells. The limulus reaction-activating substance is found to have the property of not adhering to a glass test tube and the property of stably maintaining limulus action even when it is left for a long period of time.

TABLE 1

| ITEMS | LIMULUS REACTION-ACTIVATING SUBSTANCE | ENDOTOXIN |
|---|---|---|
| PROGENICITY | − | + |
| POLYMYXIN B | 100 | 0 |
| ACID | 120.5 | 17.2 TO 43.5 |
| ALKALI | 109.0 | 1.4 TO 28.5 |
| SOLUTION STABILITY | 99.9 | 50.5 TO 86.7 |
| HEAT STABILITY | 89.0 | 4.2 TO 5.0 |
| ABILITY TO HYDROLYZE SYNTHETIC SUBSTRATE | − | − |
| ABILITY TO ACTIVATE FACTOR C | + | + |
| ANTI-FACTOR C MONOCLONAL ANTIBODY | 0 | 0 |
| ABILITY TO ACTIVATE FACTOR G | − | − |
| ABILITY TO ACTIVATE PROCLOTTING ENZYME | − | − |
| ALKALI METAL OR OTHERS | 24.6 | 100 |
| ENDOTOXIN ADSORBENT | 3.5 TO 25.6 | 3.5 TO 37.0 |
| SURFACTANT* | 0 | 81.0 TO 112.5 |

[Figures in the table represent the residual activity (%) of the substance and endotoxin.]
*see Example 2

Notes)
PYROGENICITY: A test for pyrogenicity is performed in compliance with the rabbit pyrogen test described in the Japanese Pharmacopoeia. If the value obtained by subtracting the body temperature (rectal temperature) of the rabbit measured at the starting time from the maximum body temperature measured after a lapse of three hours is greater than 0.55° C., the rabbit is considered to test positive.

POLYMYXIN B: An aqueous solution of polymyxin B sulfate (Sigma Co., Ltd., and a concentration of used polymyxin B: 0.5 mg/ml)

ACID: The substance and endotoxin are treated with 0.2M hydrochloric acid at 37° C. for 60 min.

ALKALI: The substance and endotoxin are treated with 0.2M potassium hydroxide at 37° C. for 60 min.

HEAT STABILITY: The substance and endotoxin are heated at 100° C. for 60 min.

SOLUTION STABILITY: The substance and endotoxin are left in 0.02M phosphate buffer solution (pH 7.0) at 4° C. for 10 days.

ABILITY TO HYDROLYZE SYNTHETIC SUBSTRATE: Boc-Leu-Gly-Art-pNA-HCl (the number of reacted moles: 3.0 mM)

ABILITY TO ACTIVATE FACTOR C: The ability to activate factor C is measured by means of the amidase activity against the synthetic substrate of active factor C through use of purified factor C (prepared by the method disclosed in Nakamura T. et. al., Eur. J. Biochem. 154, pp. 511 to 521 81986).

ANTI-FACTOR-C MONOCLONAL ANTIBODY: The hindrance is measured after a 250-fold dilution of mouse monoclonal antibody against factor C (2C12) has been added to a sample for limulus assay in proportions of 1:1 part by volume.

ABILITY TO ACTIVATE FACTOR G: The proclotting enzyme-activation ability is measured by means of the amidase activity against a synthetic substrate through use of purified factor G [prepared by the method disclosed in Obayashi T. et al., Clin. Chi., Acta, 149, pp. 55 to 65 (1985)].

ABILITY TO ACTIVATE PROCLOTTING ENZYME: Like the case of factor G, the ability to activate into the activated clotting enzyme of the proclotting enzyme purified by the method proposed by Obayashi et. al., is measured by means of the amidase activity against the synthetic substrate.

ALKALI METAL OR OTHERS: An aqueous solution of NaCl, KCl, MgCl$_2$, or CaCl$_2$ (the number of reacted moles: 0 to 1.5M)

ENDOTOXIN ADSORBENT: Endotoxin is brought into contact with END-X-B15 (i.e., an adsorbent it's ligand is a neutralizing factor in the limulus amebocyte; adsorbent manufactured by Capecod Co., Ltd. and available from Seikagaku Corporation), and Pyrocep A&C (i.e., an adsorbent it's ligand is histidine; adsorbent manufactured by Tanabe Seiyaku Co., Ltd. and available from Wako Pure Chemical Industries), and unadsorbed fractions are collected. The amount of endotoxin contained in the thus-collected fractions is measured by Endospecy to thereby calculate the proportion of the endotoxin adhered to a carrier (%).

EXAMPLE 2

Effect of various types of surfactants on the limulus reaction-activating substance and endotoxin 25 μl of the limulus reaction-activating substance manufactured from the influenza HA vaccine (IHA-Lot A) or the Japanese B encephalitis (JEC-Lot A) in the foregoing example and 25 μl of E. coli 0111:B4 endotoxin (Westphal type, hereinafter referred to as Et-B4, 2EU/ml) were poured into a Toxipet Plate 96F. 25 μl of nonionic surfactant solution, such as a polyoxyethylene-based surfactant (available under the trade-names Tween, Triton, Brij or the like from Sigma Co., Ltd., Aldrich Co., Ltd., Wako Pure Chemical Industries, and Dojin Kagaku Laboratories), were added to and mixed with the substance and the endotoxin well. Subsequently, 50 μl of Endospecy were added and allowed to react with the mixture at 37° C. for 30 min. As in Example 1, the residual activity of the limulus reaction-activating substance and endotoxin (%) was calculated, with distilled water taken as an unprocessed control group. From table 2, it is understood that if an appropriate concentration of surfactant is added, a great difference with regard to residual activity arises between the limulus reaction-activating substance and endotoxin, depending on the types of surfactants. For example, it is obvious that if surfactant Brij 56 is added to the limulus reaction-activating substance and endotoxin, the limulus reaction-activating substance contained in the influenza HA vaccine can be completely inactivated, whereas the activity of endotoxin is maintained suitably. As is also evident from Table 2, in addition to Brij 56, another surfactant, such as Triton N-101 or Tergitol, acts on the limulus reaction-activating substance in an analogous manner. It is found that, as a result of copresence of an aqueous solution of such surfactant in the sample, as required, the effect of the limulus reaction-activating substance mixed in the sample on the limulus reaction (i.e., the false-positive characteristics of the sample) is eliminated, and that the amount of endotoxin alone can be specifically measured.

TABLE 2

| SURFACTANT (SURFACTANT CONCENTRATION IN A MIXTURE, WEIGHT BY VOLUME) | RESIDUAL ACTIVITY (%) | |
|---|---|---|
| | LIMULUS REACTION-ACTIVATING SUBSTANCE OF THE PRESENT INVENTION | ENDOTOXIN |
| NONIONIC SURFACTANTS | | |
| Tween 20 (0.1) | 1.0 | 65.8 |
| Tween 40 (0.1) | 26.4 | 100.0 |
| Tween 60 (0.1) | 34.5 | 99.0 |
| Tween 80 (0.1) | 21.6 | 89.6 |
| Tween 85 0.1) | 1.1 | 40.2 |
| Emasol 310 | 1.0 | 78.5 |
| Triton X-100 (0.01) | 40.2 | 102.0 |
| Triton X-114 (0.01) | 1.3 | 78.1 |
| Triton X-405 (0.02) | 1.5 | 85.0 |
| Triton N-101 (0.01) | 1.0 | 92.5 |
| Triton WX-1339 (0.01) | 18.0 | 99.0 |
| Brij 30 (0.1) | 0.4 | 100.4 |
| Brij 35 (0.15) | 23.5 | 104.0 |
| Brij 52 (0.15) | 16.8 | 105.0 |
| Brij 56 (0.1) | 0 | 100.0 |
| Brij 58 (0.15) | 22.6 | 80.7 |
| Brij 92 (0.2) | 27.3 | 97.5 |
| Nonidet P-40 (0.25) | 25.0 | 98.0 |
| MEGA-10 (0.06) | 28.9 | 103.4 |
| Tergitol NP-7 (0.1) | 0.5 | 85.0 |
| AMPHOTERIC SURFACTANTS | | |
| CHAPS (0.2%) | 35.7 | 101.5 |
| CHAPSO (0.2%) | 29.4 | 100.3 |
| ANIONIC SURFACTANT | | |
| SDS (SODIUM DODECYL SULFATE) (0.005%) | 15.8 | 83.7 |

EXAMPLE 3

Effects of various types of surfactants on the measurement of the amount of endotoxin contained in each of various types of biological products 25 μl of a biological product containing a high concentration of limulus reaction-activating substance [influenza HA vaccine (IHA-Lot B, a stock solution), Japanese B encephalitis (JEC-Lot B, a stock solution), and human serum albumin (HSA-Lot Y1) prepared to a concentration of 2.5% (weight by volume)] were dispensed to separately microplates. 25 μl of Tergitol, Triton N-101, and Brij 56 (all of which are available from Sigma Co., Ltd.) solutions were added to and mixed with the respective microplates so as to produce a concentration of 0.004 to 0.25% (weight by volume). After the thus-prepared mixtures had been stirred well (at room temperature for 1 min.), 50 μl Endospecy were added to each of the mixtures. The concentration of endotoxin contained in each of the mixtures was calculated by the method described in Example 1. The amount of residual limulus reaction-activating substance, i.e., the proportion (%) residual limulus reaction-activating substance, was calculated by comparing the endotoxin concentration with that of an endotoxin-free control group (i.e., distilled water). Further, taking the endotoxin recovery (%) of distilled water as 100%, the endotoxin recovery was calculated by adding a known concentration (1.2 EU/ml) of endotoxin (Et-B4) to various types of biological products which substantially do not contain any limulus reaction-activating substance. As is evident from Table 3, if an aqueous solution of surfactant prepared to a suitable concentration is used, there can be set conditions under which nonspecific endotoxin reaction does not remain and the amount of endotoxin alone can be specifically measured. More specifically, it is understood that a superior ratio of recovery of endotoxin and the elimination of the nonspecific endotoxin activity (i.e., the response of the limulus reaction-activating substance) can be achieved by merely mixing the sample with the aqueous solution of surfactant which respectively have suitable concentrations. As a result, the amount of endotoxin alone contained in the sample can be specifically measured. From table 3, it is obvious that the foregoing objectives can be achieved by use of an aqueous solution having a suitable concentration of Brij 56 for biological product IHA; an aqueous solution having a suitable concentration of Tergitol, Triton N-101, or Brij 56 for biological product JEC; and an aqueous solution having a suitable concentration of Brij 56 for biological product HSA.

TABLE 3

| BIOLOGICAL | RESIDUAL LIMULUS ACTIVITY (EU/ml) ( ): ENDOTOXIN RECOVERY, % | | |
| --- | --- | --- | --- |
| PRODUCTS | TERGITOL | TRITON N-101 | BRIJ 56 |
| IHA | 55.3 (102.5) | 61.4 (98.5) | 16.3 (102.0) |
| JEC | 9.6 (101.2) | 10.0 (99.5) | 8.5 (100.0) |
| HSA | 91.4 (100.8) | 91.4 (99.8) | 1.4 (99.8) |

Note:
Concentrations of surfactants mixed with the sample are Tergitol: 0.01% (weight by volume), Triton N-101: 0.008% (weight by volume), Brij 56: 0.125% (Weight by volume).

EXAMPLE 4

Figure 3:
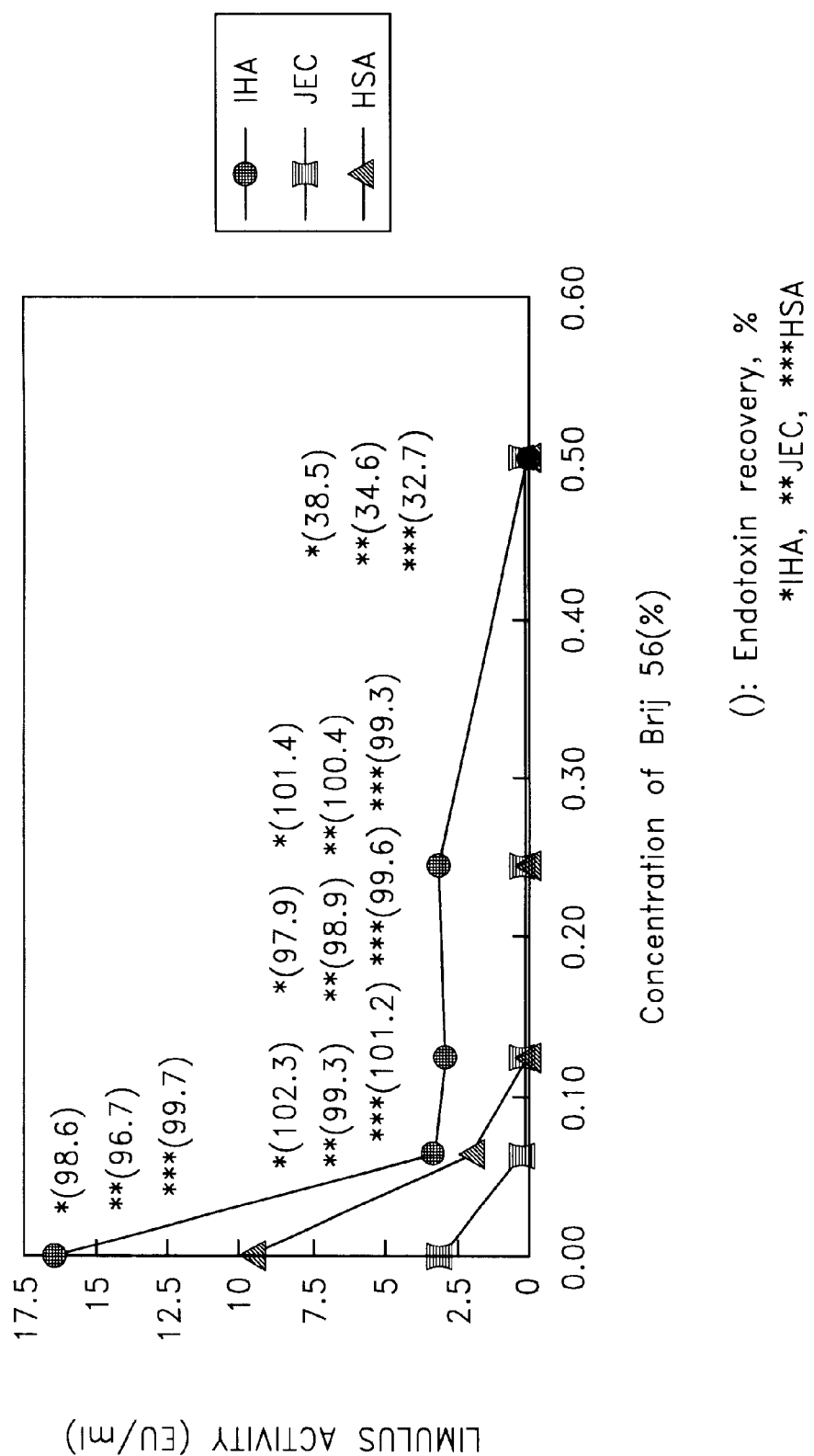
FIG. 3 is a plot showing the effects of surfactants of various concentrations during the measurement of the amount of endotoxin contained in a biological product.

Influence of Brij 56's concentration on the measurement of the amount of endotoxin contained in each of various types of biological products After 25 µl of Brij 56 solution—which was prepared in such a way as to have a concentration of 0 to 0.5% (weight by volume) when mixed with a biological product—had been added to each 25 µl of the biological products used in the Example 3, 50 µl of Endospecy was added to the biological products. The concentration of endotoxin contained in each of the biological products (EU/ml) was measured by the method described in Example 1. Concurrently, there was measured the endotoxin recovery (%) for each of the concentrations of the aqueous solutions of Brij 56. FIG. 3 shows the thus-measured endotoxin concentrations and the Brij 56 concentrations. As the concentration of the aqueous solution of Brij 56 increases, the limulus activity (i.e., the non-specific endotoxin concentrations) and the endotoxin recovery decrease significantly.

Accordingly, there is selected the concentration of Brij 56 which enables the maximum inhibition of the activity of the nonspecific endotoxin (i.e., the limulus reaction-activating substance) while the endotoxin recovery is suitably maintained, as required. It is obvious that the limulus reaction-activating substance mixed in the sample can be inactivated and the amount of endotoxin alone can be specifically measured within the thus-selected extent of concentration.

EXAMPLE 5

Figure 4:
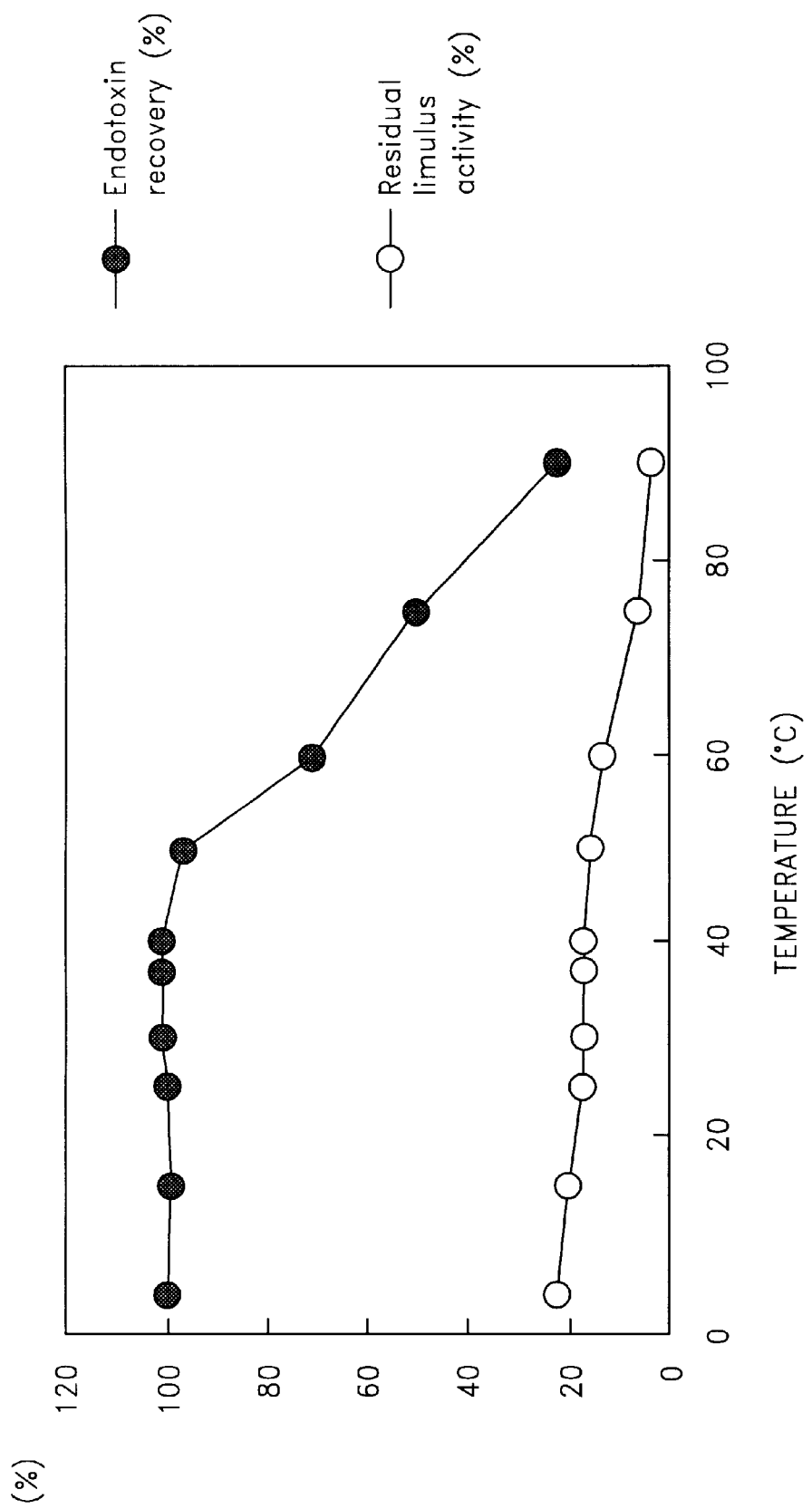
FIG. 4 is a plot showing the effects of incubation temperature at an incubation time of 1 minute after addition of a surfactant to a biological product on the measurement of the amount of the endotoxin contained in the product.

Influence of the temperature at which Brij is mixed with the sample and the time period over which the mixed sample is left after the mixing of Brij on the measurement of the amount of endotoxin contained in each of the various types of biological products The aqueous solution of Brij 56 was added to and mixed with 25 µl influenza HA vaccine (IHA-Lot B) in such a way that the concentration of Brij 56 in the mixture became 0.125%. The mixture was added at 4 to 80° C. for one min. After having been mixed further, the mixture was left at the same temperature for 1 to 20 minutes. The relative value of the activity of endotoxin [i.e., the ratio of residual limulus reaction which is obtained on the basis of distilled water being taken as a control group (having a residual limulus reaction ratio of 100%)] and the endotoxin recovery was calculated. FIG. 4 shows the results of such calculation at each temperature obtained when the mixture was stirred for one min. FIG. 4 shows that the maximum inhibition of limulus activity is achieved while a suitable endotoxin recovery is maintained by merely adding the aqueous solution of surfactant to the sample and stirring the mixture for one min. at 4 to 50° C. (i.e., the ratio of residual limulus activity and the endotoxin recovery were not particularly affected even when the mixture was left for 5 minutes at 4 to 40° C.). Additionally, under the conditions in which the mixture was heated to 60° C. or more, the activity of endotoxin was not stably maintained, thereby making is impossible to correctly measure the amount of endotoxin contained in the sample.

EXAMPLE 6

Figure 5A:
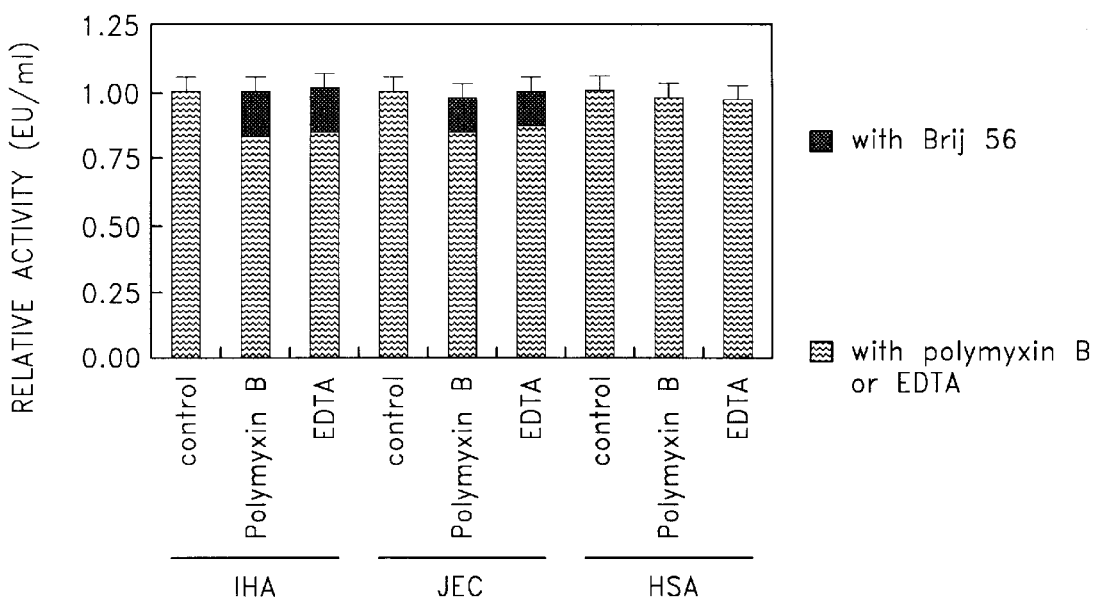
FIGS. 5A and 5B are plots showing the effect of polymyxin B, EDTA-4Na, and a surfactant on the measurement of the amount of endotoxin.
Figure 5B:
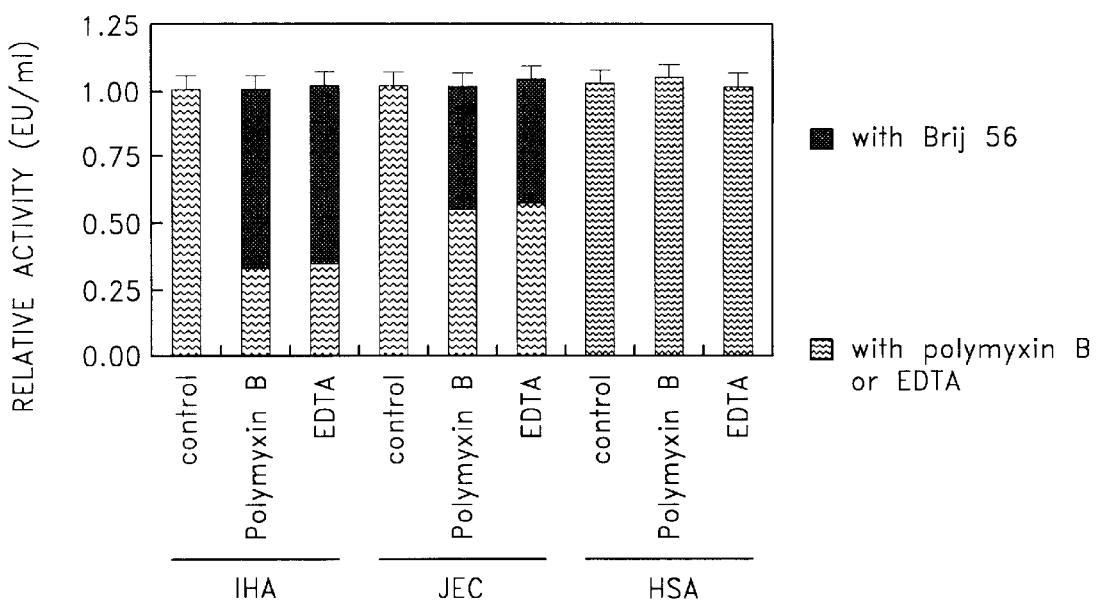

Influence of Polymyxin B, EDTA-4Na, and Brij 56 on the measurement of the amount of endotoxin contained in each of various types of biological products A total of six lots of 25 µl of preparations containing biological products similar to those used in Example 3 were mixed with 25 µl of Polymyxin B sulfate (available from Sigma Co., Ltd., 2 mg/ml) solution, 25 µl of EDTA-4Na solution, or 25 µl of 0.25% (weight by volume) Brij 56 solution. 50 µl of Endospecy was added to each mixture, and the concentration of endotoxin (EU/ml) in the thus-prepared mixture was measured in the same way as in Example 1. Provided that a control group (a total amount of endotoxin and the limulus reaction-activating substance) without addition of polymyxin B, EDTA-4Na, or Brij 56 is taken as 1, the activity ratio of the mixture to the control group was calculated under various conditions. Assuming that the endotoxin contained in the sample alone is specifically inactivated by addition to the biological products of the polymyxin B or EDTA-4Na solution having a predetermined concentration, and the limulus reaction-activating substance contained in the sample alone is specifically inactivated by addition of Brij 56 to the biological products, the sum of the ratio of an endotoxin concentration and a limulus reaction-activating substance concentration obtained as a result of addition of the surfactant to the biological product to the control must represent a total amount of endotoxin and the limulus reaction-activating substance. As is evident from FIGS. 5A and 5B (a similar test was performed through use of other lots), in each of the biological products, the sum of the endotoxin concentration and the limulus reaction-activating substance concentration was 1 (0.05 (CV=5%, n=3). The hypothesis was proved to be correct. From this fact, it is understood that the limulus reaction-activating substance alone can be inactivated and the amount of endotoxin can be specifically measured by solely bringing the Brij 56 solution in copresence with the sample in a given concentration.

EXAMPLE 7

Figure 6A:
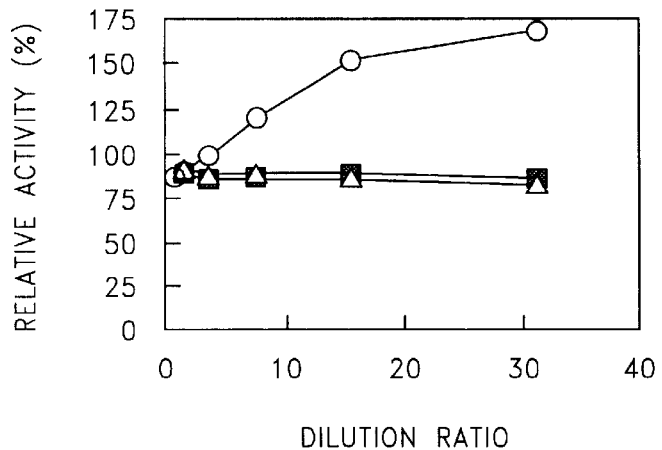
FIGS. 6A to 6C are plots showing dilution dose responses.
Figure 6B:
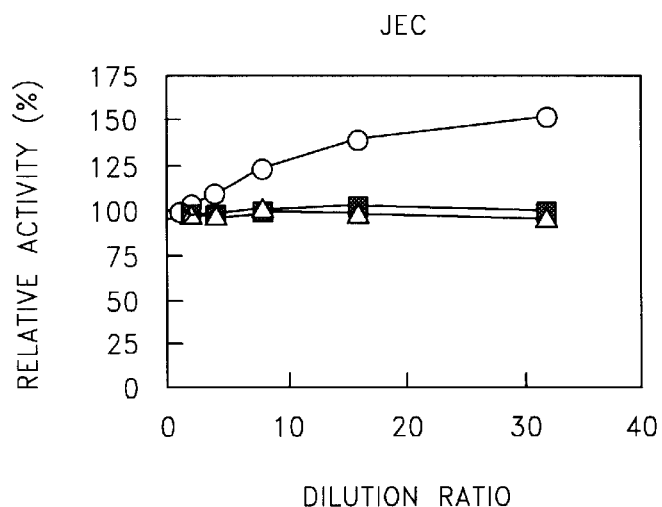
Figure 6C:
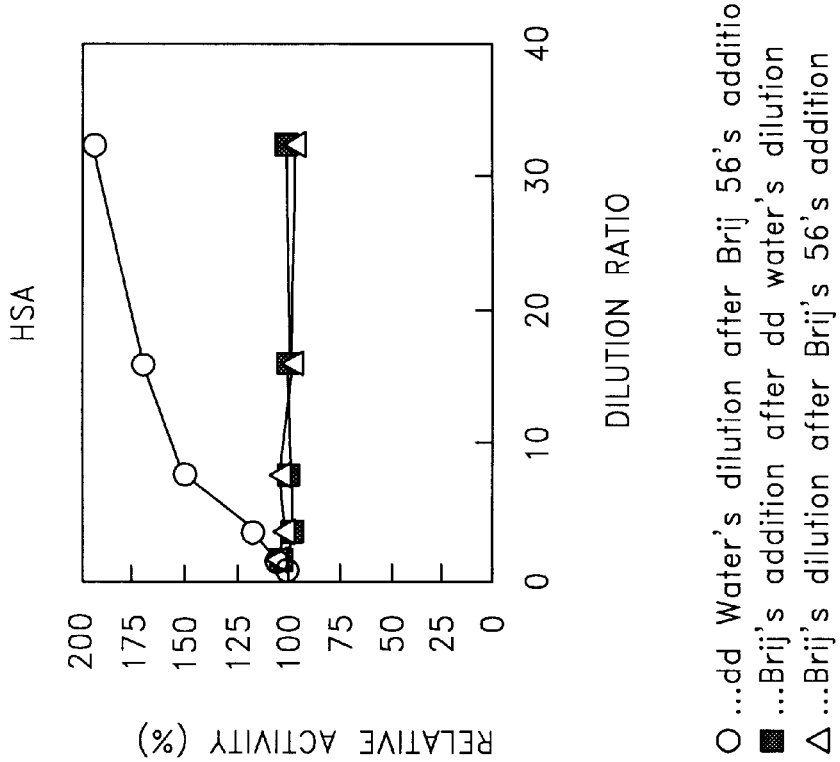

Dilution dose responses of various types of biological products 0.25% (weight by volume) Brij 56 solution were added in an equivalent amount to biological products similar to those used in Example 3. 25 μl of the solution—which was diluted 2 to 32 fold with distilled water or 0.125% Brij 56 solution—and 25 μl of the solution—which was diluted 2 to 32 fold with distilled water in advance—were poured into each of the Toxipet Plates 96F. Distilled water and 25 μl of 0.25% (weight by volume) Brij 56 solution were added to the respective plates and stirred well. 50 μl of Endospecy were added to the plates, and the concentration of endotoxin contained in the thus-prepared mixture on each plate was measured by the method described in Example 1. Each of the thus-measured endotoxin concentrations was divided by a true amount of endotoxin, i.e., a measured value obtained by adding 25 μl of 0.25% (weight by volume) Brij 56 solution to 25 μl of the sample, to thereby obtain a relative activity (%). The thus-obtained relative activities were plotted for each of dilution ratios. As shown in FIGS. 6A to 6C, as for the sample that is diluted with distilled water in advance and to which the Brij 56 solution was then added, stable relative activity was obtained in each of the dilution ratios. But the sample that diluted with distilled water after addition of the Brij 56 solution showed tendency that the relative activity was rising with the increase of dilution rate. The Brij 56 solution was added to the sample, and this sample was then diluted with 0.125% (weight by volume) Brij 56 solution in place of distilled water. As a result, the stable relative activity was obtained, as in the case where the Brij 56 solution was added to the sample, and a suitable dilution dose response is acknowledged. The reversible recovery of part of the activity of the limulus reaction-activating substance inactivated by Brij 56 was observed by addition of distilled water so as to dilute the limulus reaction-activating substance (i.e., by dilution of the concentration of Brij 56 in the sample). In contrast, such a recovery phenomenon was not observed at all in the sample which was inactivated by Brij 56 and diluted with Brij 56 to the same concentration as that of the inactivated sample. A constant endotoxin concentration is obtained for any dilution ratio.

in this respect, the limulus reaction false-positive substance of the present invention is significantly different in properties from known limulus reaction false-positive substances, and the method of inactivating the limulus reaction-activating substance of the present invention is greatly different from the existing method of inactivating a limulus reaction false-positive substance produced predominantly from blood used as a sample for limulus assay. It is known that once the false-positive substance has been inactivated, the limulus activity of the substance is not recovered at all even if the substance undergoes treatment.

The limulus-reaction-activating-ability of the limulus reaction-activating substance of the present invention is inhibited only when it coexists with a specific surfactant having a given concentration. Accordingly, in a case where a true amount of endotoxin contained in the sample is correctly measured by elimination of the effect of the limulus reaction-activating substance, the substance must be constantly held in copresence with the specific surfactant having a given concentration. In this respect, the endotoxin measurement method of the present invention is significantly different from the existing endotoxin measurement method associated with the method of inactivating a limulus reaction false-positive substance or the like.

EXAMPLE 8

Measurement of endotoxin contained in a biological product through use of various types of limulus reagents 0.3% (weight by volume) Brij 30 solution was added in an equivalent amount to each of the various types of biological products used in Example 3, and Endospecy or various types of limulus reagents were added to the biological products. The concentration of endotoxin (EU/ml) contained in each of the thus-prepared samples for limulus assay was measured through use of standard endotoxin ET-B4. The results of such measurement are provided in Table 4.

TABLE 4

| BIOLOGICAL PRODUCTS | CONDITIONS | LIMULUS REAGENTS FROM DIFFERENT MANUFACTURERS | | | |
|---|---|---|---|---|---|
| | | A | B | C | D |
| IHA | NONE | 20.0 | 21.0 | 25.6 | 28.5 |
| | Brij 30 | 4.0 | 4.1 | 3.9 | 4.3 |
| JEC | NONE | 3.8 | 4.2 | 4.8 | 5.0 |
| | Brij 30 | 0.4 | 0.4 | 0.4 | 0.5 |
| HSA | NONE | 10.2 | 10.8 | 12.4 | 13.0 |
| | Brij 30 | 0 | 0 | 0.1 | 0.2 |

A: ENDOSPECY (KINETIC COLORIMETRY)
B: LIMULUS ES-II TEST WAKO (KINETIC TURBIDIMETRY)
C: KINETIC QCL SYSTEM (KINETIC COLORIMETRY)
D: PYROTEL-T (KINETIC TURBIDIMETRY)

After the Brij 30 solution had been added to the samples, the concentration of endotoxin contained in each of the samples was measured through use of various types of limulus reagents. As can be seen from Table 4, every sample shows a substantially similar tendency. It is obvious that the amount of endotoxin alone can be specifically measured by merely bringing Brij 30 into copresence with the sample even when another measurement method and another measurement reagent are used.

EXAMPLE 9

Effect of an alkylamine on endotoxin response

Figure 7A:
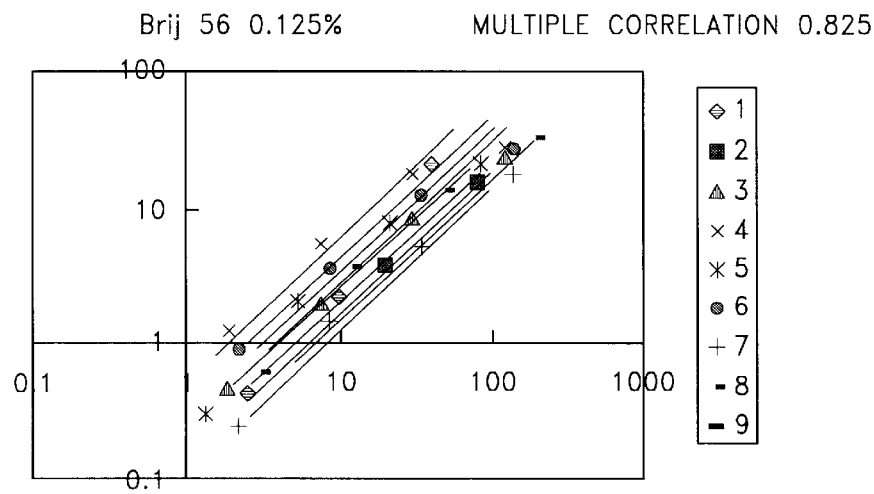
FIGS. 7A and 7B show the effect of a surfactant and triethylamine on various endotoxin responses (in distilled water)
Figure 7B:
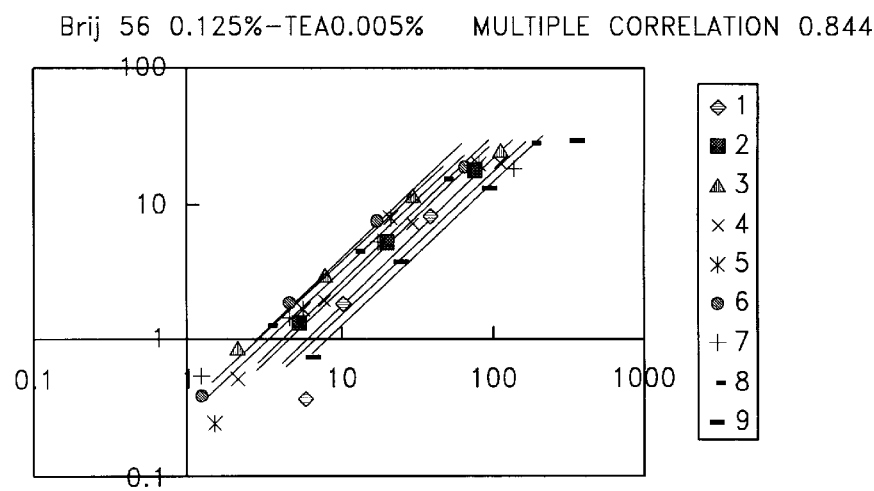

25 μl of Brij 56 solution (0.25%) were added to each of water-dilution steps (n=9), each step having a quantity of 25 μl, for each of various B- and R-types endotoxin solutions which are different from each other primarily with regard to the chain length of O-antigen polysaccharide (E. coli 0111:B4 three types, E. coli UKT-B, E. coli 0113, Salmonella minnesota R595, S. minnesota R5(Rc), S. typhosa, S. enteritidis). 50 μl of Endospecy were added to each of the thus-produced mixtures, and the concentration of endotoxin (EU/ml) in each of the mixtures was measured by the method described in the Examples. The thus-measured endotoxin concentrations are represented in the form of a log-log plot. As a result, there arises a tendency to show a different titer according to the type of endotoxin. As shown in FIGS. 7A and 7B, the irregularities in the titer are properly converged by adding triethylamine to the Brij 56 solution to a concentration of 0.005% (weight by volume) in advance (a multiple correlation of 0.844). Similarly, the dose dependency of endotoxin was checked by adding various types of endotoxin to influenza HA vaccine (IHA-Lot M) which is substantially free from endotoxin. As shown in FIGS. 8A and 8B, in comparison with the case where endotoxin coexists solely with Brij 56, a superior convergence of titer lines (a multiple correlation of 0.850) is obtained in the case where triethylamine is added to the Brij 56 solution. Accordingly, it has become evident that the dispersed state of endotoxin is properly maintained by adding triethylamine having a predetermined concentration to the Brij 56 solution to thereby minimize the difference in reactivity between endotoxin owing to solubility or the type of fungus to as small as extent as possible, and that the amount of endotoxin contained in the sample can be more correctly measured.

EXAMPLE 10

Measurement of the amount of endotoxin in each of various types of biological products by means of Parallel line assay 25 μl of Brij mixture packed into a kit [0.25% (weight by volume) Brij 56+0.010% (weight by volume) triethylamine] were added to each of a series of distilled water-diluted solution (N=4)—each solution having a volume of 25 μl—for each of three types of biological products (IHA-Lot D, JEC-F, HSA-Y2. The mixtures were then stirred. 50 μl of Endospecy attached to the kit was added to the mixtures, and the mixtures were brought into reaction at 37° C. for 30 min. in a Well Reader SK601. The rate of changes (mAbs405-492 nm/min.) in the absorbance per minute was analyzed through use of parallel determination software (available under tradename RG301 from Seikagaku Corporation). The concentration of endotoxin (EU/ml) was calculated through use of standard endotoxin of the Japanese Pharmacopoeia (*E. coli* UKT-B). As shown in FIG. 9, suitable parallel lines and reproducibility were obtained for each of the preparations. The kit was able to specifically and accurately determine the amount of endotoxin contained in the biological products.

EXAMPLE 11

Measurement of the limulus reaction-activating substance in each of various types of biological products 0.2M NaOH was added in an equivalent amount to each 50 μl of the various types of biological products described in Example 8. After the preparations had been heated at 37° C. for one hr., 50 μl of 0.2M HCl were added so as to neutralize the mixtures. (A) 50 μl of Endospecy were added to the thus-neutralized mixtures and brought into reaction at 37° C. for 30 min., and the amount of the limulus reaction-activating substance was measured. In contrast, there were measured (C) a total amount of the endotoxin and limulus reaction-activating substance measured through use of distilled water in place of NaOH and (B) the amount of endotoxin measured by adding 25 μl of 0.25% Brij 56 to 25 μl of the preparations and subsequently adding 50 μl of Endospecy to the same. All these amounts are provided in Table 5.

As shown in Table 5, even in the case of each of IHA, JEC, HSA preparations, the amount of the limulus reaction-activating substance mixed in the preparations alone can be specifically measured by merely adding NaOH to the preparation and heating at 37° C. The value obtained by adding the measured value (B) of endotoxin obtained by adding aqueous solution of the Brij 56 and Endospecy to the preparation to the measured value (A) of the limulus reaction-activating substance obtained by the foregoing method is substantially equivalent to the measured value (C) of the total amount of endotoxin and the limulus reaction-activating substance. Therefore, it is evident that the measurement method of the present invention enables correct measurement of the amount of limulus reaction-activating substance.

TABLE 5

| BIOLOGICAL | CONDITIONS | | | |
| --- | --- | --- | --- | --- |
| PRODUCTS | A | B | C | ( ):A + B |
| IHA | 14.0 | 3.0 | 17.3 | (17.0) |
| JEC | 2.9 | 0.2 | 3.2 | (3.1) |
| HSA | 9.4 | 0 | 9.3 | (9.4) |

As has been described above, the present invention provides a method of readily and quickly inactivating a non-endotoxin limulus reaction-activating substance which is mixed in a biological product and does not have pyrogenic characteristics, and of accurately measuring the amount of endotoxin alone through use of a limulus reagent.

By virtue of the present invention, the amount of endotoxin in the biological product is correctly measured, and therefore the evaluation of safety of biological products can be performed more suitably, representing a great contribution to medical care. Further, since the limulus reaction-activating substance has physical properties similar to those of endotoxin, physiological properties and toxicity present new problems in the future.

The method of measuring the amount of endotoxin and the limulus reaction-activating substance of the present invention possesses great medical significance.

We claim:

1. A method of inactivating a limulus reaction-activating substance in a biologically-processed product, excluding whole blood product and blood fractions, said method comprising the steps of:

selecting an inactivating agent comprising a surfactant having a freezing point and being capable of inactivating a limulus reaction-activating substance, said limulus reaction-activating substance having the following characteristics:
(a) exhibiting limulus reaction activity;
(b) reactive with an endotoxin-specific limulus reagent;
(c) activating factor C of an amebocyte lysate of a horseshoe crab;
(d) exhibiting no pyrogenicity by a rabbit pyrogen test;
(e) exhibiting no endotoxic activity;
(f) exhibiting no (1→3)-β-D-glucan activity;
(g) exhibiting no serine protease activity;
(h) maintaining the limulus reaction activity when coexisting with polymyxin B;
(i) maintaining the limulus reaction activity when coexisting with colistin;
(j) maintaining the limulus reaction activity when being exposed to 0.2M hydrochloride acid at 37° C. for 60 min.;
(k) maintaining the limulus reaction activity when being exposed to 0.2M potassium hydroxide at 37° C. for 60 min.;
(l) reducing the limulus reaction activity when being exposed to polyxyethylene hexadecylether;

selecting a temperature for inactivating the limulus reaction-activating substance by the inactivating agent, said temperature ranging from the freezing point of the surfactant to 50° C.; and contacting the inactivating agent with the limulus reaction-activating substance, if any, in the biologically-processed product until the limulus reaction-activating substance is inactivated.

2. A method according to claim 1, wherein said inactivating agent further comprises an alkylamine.

3. A method according to claim 1, wherein said surfactant is a nonionic surfactant.

4. A method according to claim 3, wherein said nonionic surfactant is at least one selected from the group consisting of polyoxyethylene alkyl ether, polyoxyethylene alkylphenyl ether, and acylpolyoxyethylene sorbitan.

5. A method of measuring endotoxin present in a biologically-processed product, excluding whole blood and blood fractions, said method comprising the steps of:

selecting an inactivating agent comprising a surfactant having a freezing point and being capable of inactivating a limulus reaction-activating substance, said limulus reaction-activating substance having the following characteristics:
(a) exhibiting limulus reaction activity;
(b) reactive with an endotoxin-specific limulus reagent;
(c) activating factor C of an amebocyte lysate of a horseshoe crab;
(d) exhibiting no pyrogenicity by a rabbit pyrogen test;
(e) exhibiting no endotoxic activity;
(f) exhibiting no (1→3)-β-D-glucan activity;
(g) exhibiting no serine protease activity;
(h) maintaining the limulus reaction activity when coexisting with polymyxin B;
(i) maintaining the limulus reaction activity when coexisting with colistin;
(j) maintaining the limulus reaction activity when being exposed to 0.2M hydrochloride acid at 37° C. for 60 min.;
(k) maintaining the limulus reaction activity when being exposed to 0.2M potassium hydroxide at 37° C. for 60 min.;
(l) reducing the limulus reaction activity when being exposed to polyxyethylene hexadecylether;

selecting a temperature for inactivating the limulus reaction-activating substance by the inactivating agent, said temperature ranging from the freezing point of the surfactant to 50° C.;

contacting the inactivating agent with the limulus reaction-activating substance, if any, in the biologically-processed product until the limulus reaction-activating substance is inactivated; and measuring endotoxin using a limulus reagent.

6. A method according to claim 5, wherein said inactivating agent further comprises an alkylamine.

7. A method according to claim 5, wherein said surfactant is a nonionic surfactant.

8. A method according to claim 7, wherein said nonionic surfactant is at least one selected from the group consisting of polyoxyethylene alkyl ether, polyoxyethylene alkylphenyl ether, and acylpolyoxyethylene sorbitan.

9. A method according to claim 5, wherein said limulus reagent is an endotoxin-specific limulus reagent.

10. A method according to claim 2, wherein the alkylamine is included in the inactivating agent in an amount such that the final concentration of the alkylamine is in the range of 0.0001% to 0.05% when the limulus reaction-activating substance is contacted with the inactivating agent.

11. A method according to claim 2, wherein said alkylamine is triethylamine.

12. A method according to claim 1, wherein said biologically-processed product is selected from the group consisting of vaccine preparations, purified blood products, and antibiotics.

13. A method according to claim 5, wherein said biologically-processed product is selected from the group consisting of vaccine preparations, purified blood products, and antibiotics.

14. A method according to claim 5, wherein the step of measuring endotoxin is conducted without removing the surfactant.

* * * * *